United States Patent [19]
Wang et al.

[11] Patent Number: 5,461,570
[45] Date of Patent: Oct. 24, 1995

[54] COMPUTER SYSTEM FOR QUALITY CONTROL CORRELATIONS

[75] Inventors: Daniel T. Wang, Jacksonville; Lars W. Johnson, Indialantic; John M. Lepper, Jacksonville; Wallace A. Martin, Orange Park; Leonard R. Reinhart, Melbourne; Ravi S. Sanka; Craig W. Walker, both of Jacksonville, all of Fla.

[73] Assignee: Johnson & Johnson Vision Products, Inc., Jacksonville, Fla.

[21] Appl. No.: 257,800

[22] Filed: Jun. 10, 1994

[51] Int. Cl.⁶ .................................................. G06F 19/00
[52] U.S. Cl. ...................... 364/468; 364/131; 364/551.01; 364/552
[58] Field of Search ............................ 364/468, 478, 364/401–403, 131–134, 138, 139, 473, 476, 552, 525, 474.11, 550, 551.01, DIG. 1 MS FILE, DIG. 2 MS FILE; 264/1.1, 1.4, 1.6, 2.6, 40.1; 425/808, 162, 169; 395/600

[56] References Cited

U.S. PATENT DOCUMENTS

| | | | |
|---|---|---|---|
| 4,408,291 | 10/1983 | Gunzberg et al. | 364/468 X |
| 4,495,313 | 1/1985 | Larsen | 523/106 |
| 4,565,348 | 1/1986 | Larsen | 249/122 |
| 4,640,489 | 2/1987 | Larsen | 249/122 |
| 4,680,336 | 7/1987 | Larsen et al. | 264/1.4 X |
| 4,691,820 | 9/1987 | Martinez | 206/205 |
| 4,889,664 | 12/1989 | Kindt-Larsen et al. | 264/2.6 |
| 4,956,783 | 9/1990 | Teranishi et al. | 364/478 X |
| 4,980,993 | 1/1991 | Umezaki | 51/165.71 |
| 5,039,459 | 8/1991 | Kindt-Larsen et al. | 264/2.6 |
| 5,080,839 | 1/1992 | Kindt-Larsen | 264/2.6 |
| 5,094,609 | 3/1992 | Kindt-Larsen | 425/445 |
| 5,134,574 | 7/1992 | Beaverstock | 364/552 X |
| 5,339,257 | 8/1994 | Layden et al. | 364/552 |

*Primary Examiner*—Joseph Ruggiero

[57] ABSTRACT

A computer control system for optimizing process parameters in an automated production line for producing contact lenses. The system comprises a plurality of process controllers for controlling one or more process stations of the production line, each of the controllers regulating a plurality of process control devices that each control specific production parameters used in the automated manufacture of contact lenses at the process station(s). An automated lens inspection device automatically evaluates each contact lens produced and generates inspection data for each contact lens, and a polling device polls each of the process controllers on a frequent basis to acquire process control data for each period. Further included is a correlating device for correlating the inspection data to the process control data and the contact lens data to optimize process parameters used in the production of contact lenses. A relational database is also provided for storing the process control data, the contact lens data and the inspection data received from the correlating device.

30 Claims, 27 Drawing Sheets

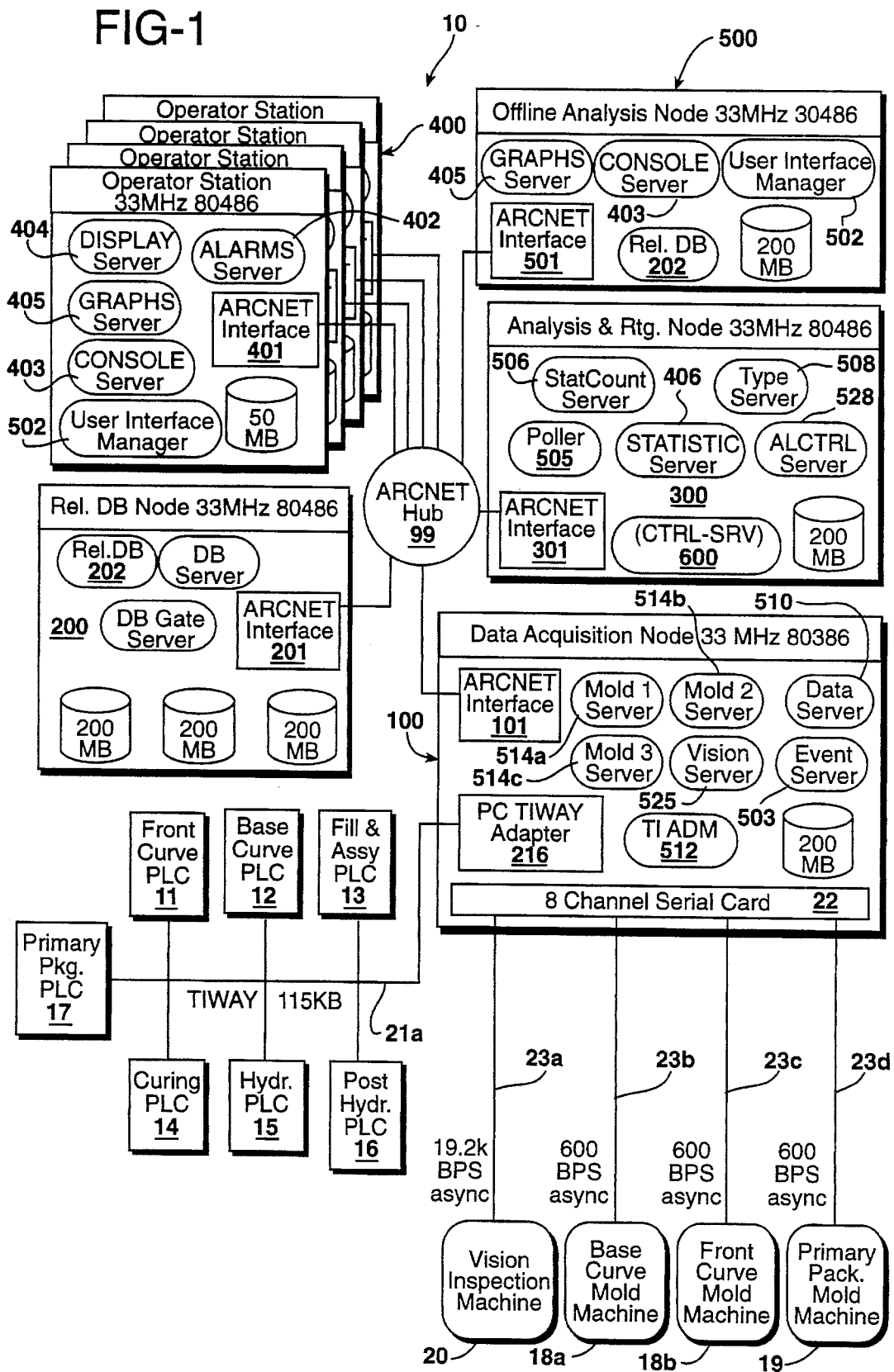

| CODE | INFORMATION ITEM |
|---|---|
| LN | Lens Number (1-16) |
| FF | Pass = 1, Fail = 0 |
| ID | Inner Defects |
| IS | Inner Score |
| OD | Outer Defects |
| OS | Outer Score |
| CD | Combo Defects |
| CS | Combo Score |
| TS | Total Score |
| CL | Center Lens Inspection Code |

FIG. 5a

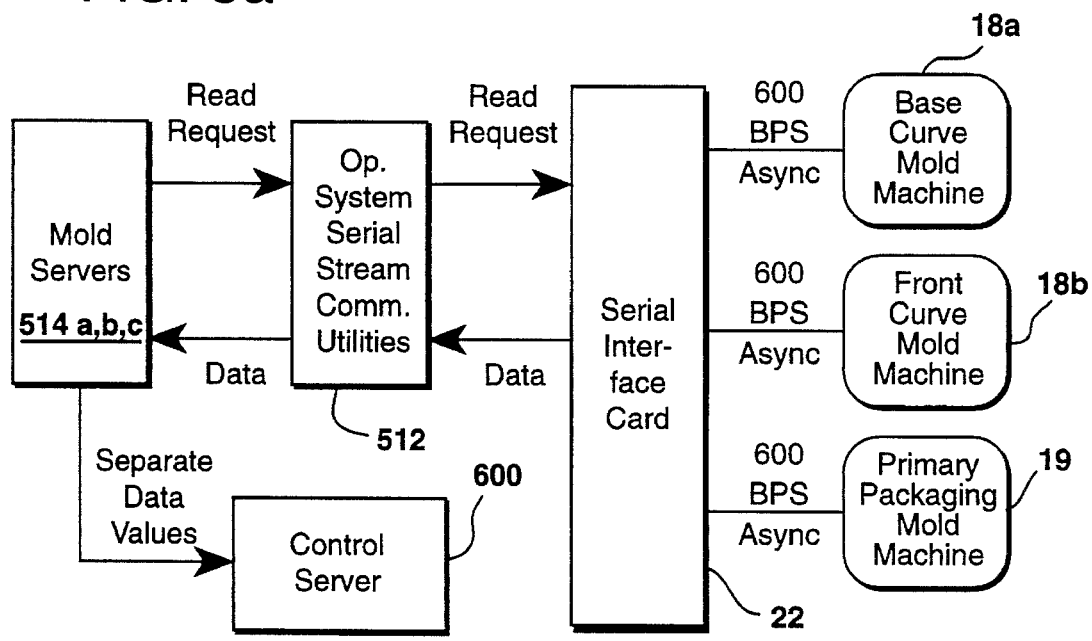

FIG. 5b

| | CODE | INFORMATION ITEM |
|---|---|---|
| 61 | TIME | Timestamp. This is NOT sent to Control Server |
| 62 | COUNT | Number of lenses produced |
| 63 | T300 | Cycle Time |
| 64 | T302 | Plasticizing Time |
| 65 | T301 | Filling Time |
| 66 | P300 | Injection Peak Pressure |
| • | S302 | Injector Start Position |
| • | S301 | V-P Switchover |
| • | S303 | Cushion Position |
| • | S304 | Pressure Hold End Position |
| • | NGMRK | 0=Off, 1=Good, 2=Bad |
| 67 | MOLD 1 | #1 Mold Temperature |
| 68 | MOLD 2 | #2 Mold Temperature |
| | MELT | Melt Temperature |

FIG. 7

| Data Source | Location In Source | Point Description |
|---|---|---|
| FC-PLC | 001 | Bit 16 Is Data Valid Flag |
| FC-PLC | 002 | Event Counter |
| FC-PLC | 003 | Most Recent Event Code |
| FC-PLC | 004 | 2nd Recent Event Code |
| FC-PLC | 005 | 3rd Recent Event Code |
| FC-PLC | 006 | 4th Recent Event Code |
| FC-PLC | 007 | 5th Recent Event Code |
| FC-PLC | 008 | 6th Recent Event Code |
| FC-PLC | 009 | 7th Recent Event Code |
| FC-PLC | 010 | 8th Recent Event Code |
| FC-PLC | 011 | 9th Recent Event Code |
| FC-PLC | 012 | 10th Recent Event Code |
| FC-PLC | 013 | Bit 16 Is Data Valid Flag |
| FC-PLC | 014 | Transfer Cycle Counter |
| FC-PLC | 015 | Part Count of FC's Deliv |
| FC-PLC | 016 | Reject Count of FC's |
| FC-PLC | 017 | Elapsed Time FC's Expos |
| FC-PLC | 018 | Cycle Time of Yushin |
| FC-PLC | 019 | Cycle Time of Linear Sld |
| FC-PLC | 020 | Cycle Time of Adept |
| FC-PLC | 021 | Spare |
| FC-PLC | 022 | Spare |
| FC-PLC | 023 | Spare |
| FC-PLC | 024 | Spare |

Rows 001–012: 78
Rows 013–024: 79

FIG. 11
| | 657a | 657b | 657c | 657d | | | |
|---|---|---|---|---|---|---|---|
| 1 | Date/Time | Bar Code Index | Label | Source Data Value1 | Source Data Value 2 | •••• | Source Data Value J |
| 2 | Date/Time | Bar Code Index | Label | Source Data Value1 | Source Data Value 2 | •••• | Source Data Value J |
| • | • | • | | • | • | • | • |
| • | • | • | | • | • | • | • |
| • | • | • | | • | • | • | • |
| n | Date/Time | Bar Code Index | Label | Source Data Value1 | Source Data Value 2 | •••• | Source Data Value J |
FIG. 13a
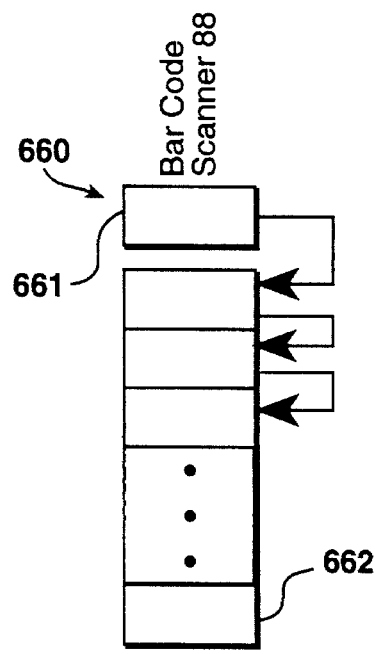
FIG. 13b
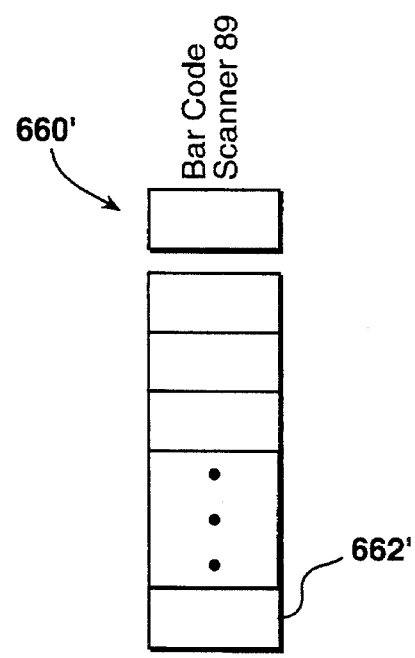

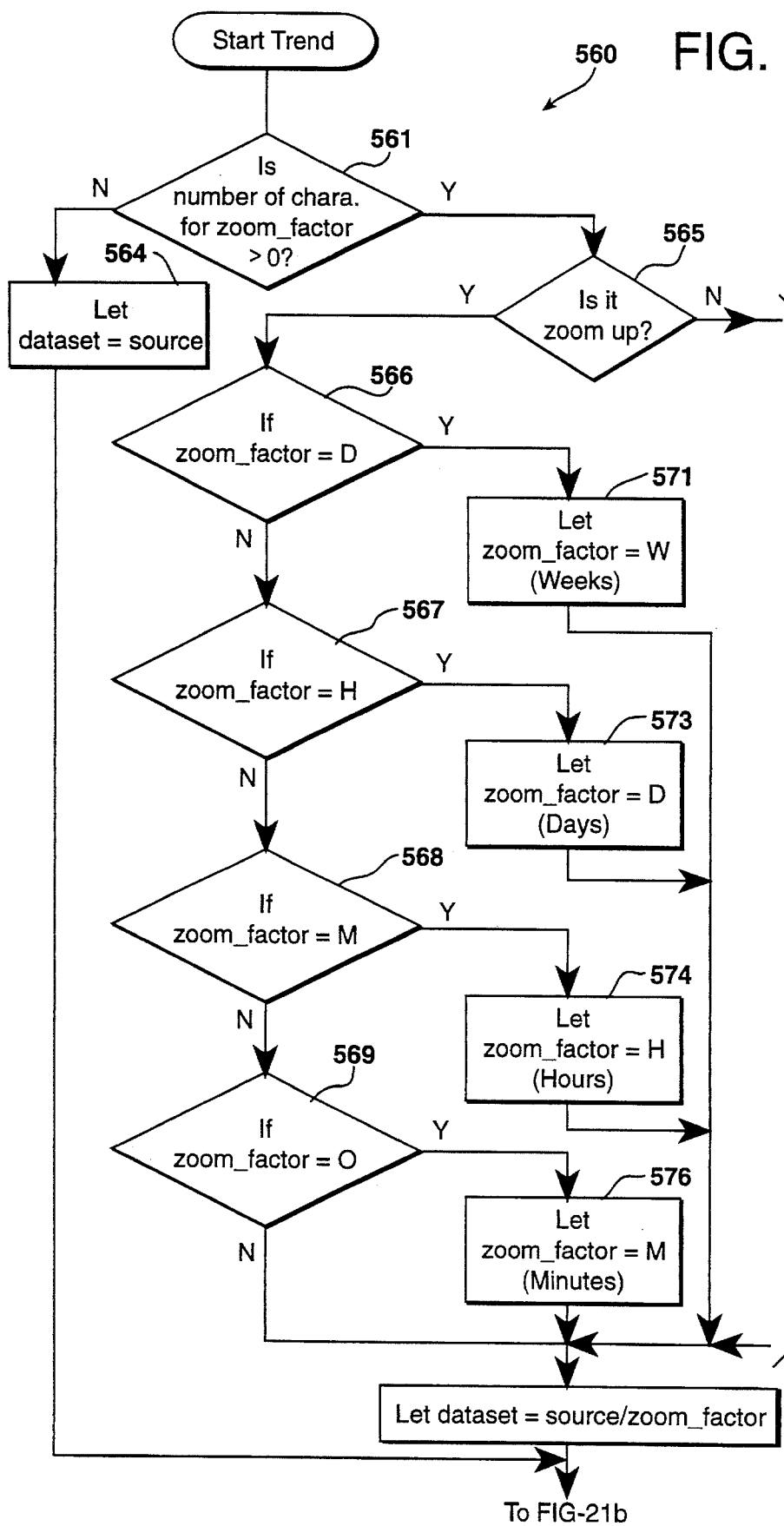
FIG. 21a(1)

FIG. 21a(2)
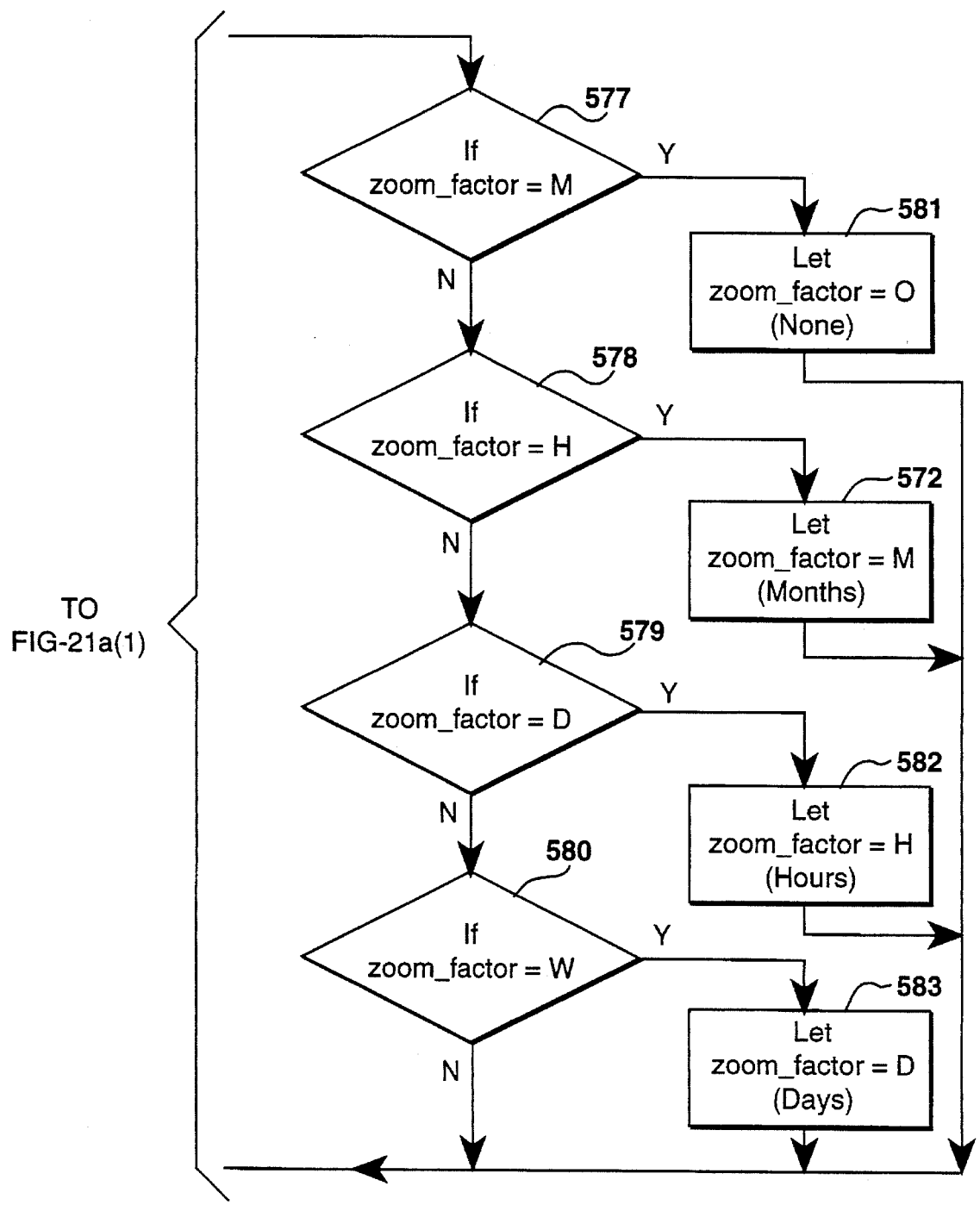

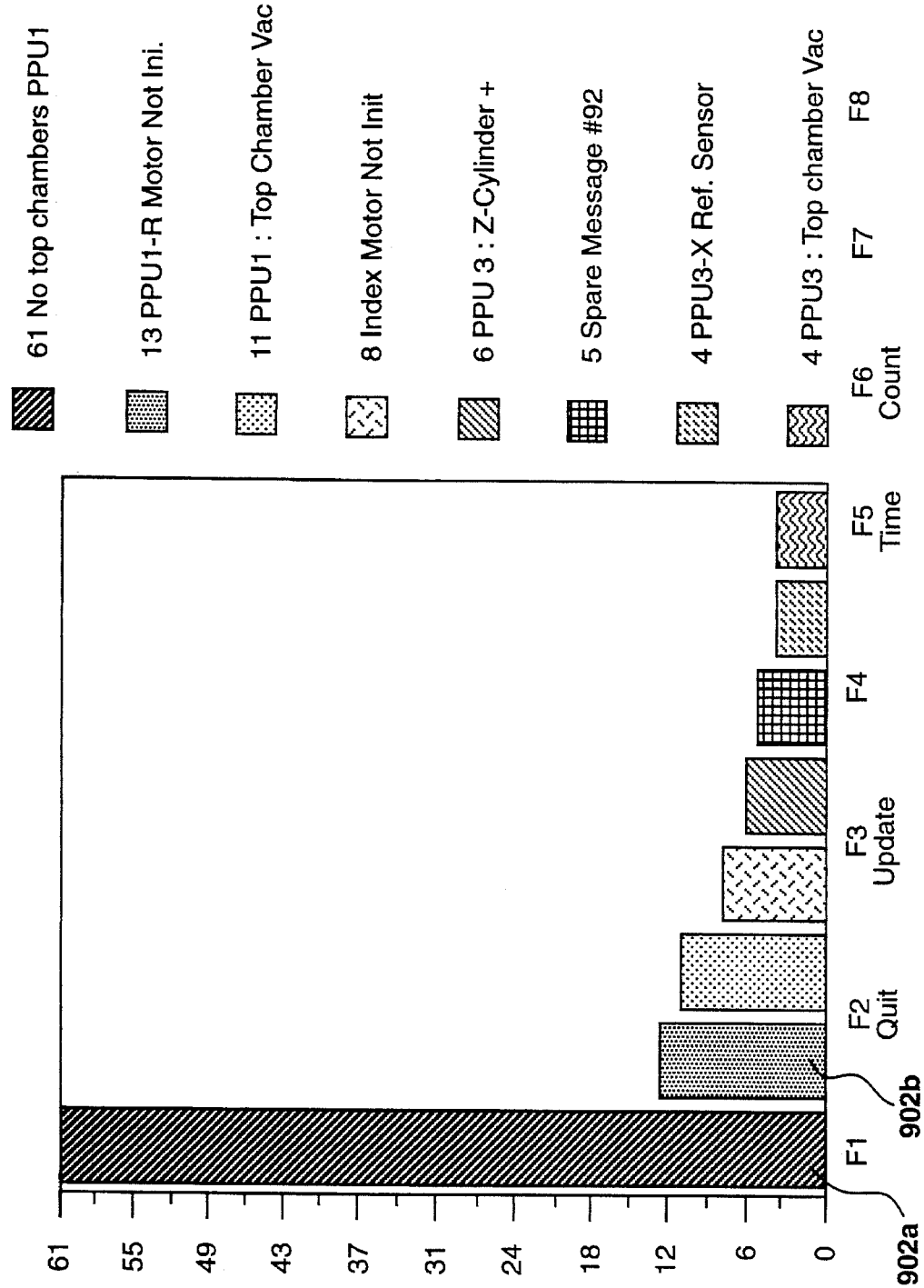

COMPUTER SYSTEM FOR QUALITY CONTROL CORRELATIONS

FIELD OF THE INVENTION

This invention relates generally to a manufacturing facility for the production of ophthalmic contact lenses, and, in particular to a supervisory system for monitoring the production line processes used in the manufacture of contact lenses in a contact lens fabrication facility, with the goal of investigating and optimizing the manufacturing process.

DESCRIPTION OF THE PRIOR ART

The direct molding of hydrogel contact lenses is disclosed in U.S. Pat. Nos. 4,495,313 to Larsen, 4,680,336 to Larsen et al., 4,565,348 to Larsen, and 4,640,489 to Larsen et al., the entire disclosures of which are hereby incorporated by reference in this patent application. Essentially, these references disclose an automated contact lens production process wherein each lens is formed by sandwiching a monomer between back curve (upper) and front curve (lower) mold sections. The monomer is polymerized, thus forming a lens, which is then removed from the mold sections and further treated and packaged for consumer use.

The manufacturing of contact lenses requires tightly controlled conditions and processes, many of which are monitored by computers and other control devices. Much information, in the form of process conditions and control data, for e.g., that occur during contact lens manufacturing, may be gathered for quality control purposes. However, this entails the acquisition of a tremendous amount of data for each contact lens that is produced, and, additionally, requires a means for processing the data acquired in a way that is suitable for use by operators, engineers, and supervisors, etc., so that they may properly perform their functions. Additionally, some of the information generated may be by human observation, for instance, lens inspection, which is not as reliable as automatic sensors.

There is therefore the need to provide a quality control system that can automatically acquire process control data from a plurality of manufacturing process controllers that control various aspects of contact lens production at process stations in a contact lens manufacturing facility, and, that can automatically process the data for real-time display and archiving purposes.

It would additionally be highly desirable to provide a quality control system that can automatically gather process control data for each specific contact lens at each of the plurality of process stations.

Additionally, it would be highly desirable to provide a quality control system that gathers process control data for each specific contact lens, and, includes means for automatically correlating the data acquired with each individual contact lens produced for storage and optimization purposes.

It would furthermore be highly desirable to provide a quality control system in a contact lens manufacturing facility that enables an operator to determine the specific reason as to why a contact lens that has been rejected during an automatic inspection process occurring subsequent to the manufacture of the lens, was flawed.

SUMMARY OF THE INVENTION

An object of the instant invention is to provide a quality control system for a contact lens manufacturing facility that automatically acquires process control data from a plurality of manufacturing process controllers that control contact lens production, and, that can automatically process the data for real-time display and off-line analysis purposes.

Another object of the invention is to provide a quality control system that gathers process control data in machine cycle time increments for each specific contact lens that is being produced.

Additionally, another object of the invention is to provide a quality control system that gathers process control data for each lens at each manufacturing process station of a contact lens production line, and includes automatic means for correlating the data acquired with each specific contact lens produced and automatically storing the data in a relational database for prospective and retrospective analysis.

Still another object is to provide a quality control system in a contact lens manufacturing facility having an automatic lens inspection system for determining flawed lenses wherein the quality control system includes means for correlating the data acquired for each specific flawed contact lens produced, and enabling the determination of the source of a particular failure for a particular lens so that production process controls may be corrected and optimized.

The above objects are achieved in a quality control system for optimizing process parameters in an automated production line for producing contact lenses. The system comprises a plurality of process control means for controlling one or more process stations of the production line, each of the control means regulating a plurality of process control devices that each control specific production parameters used in the automated manufacture of contact lenses at the process station(s). Also provided is an automated lens inspection means for automatically evaluating each contact lens produced and generating inspection data for each contact lens, and a polling means for polling each of the process control means on a periodic basis to acquire process control data for each period. Further included is a means for correlating the inspection data to the process control data and the contact lens data to optimize process parameters used in the production of contact lenses, and a relational database for storing the process control data, the contact lens data and the inspection data received from the correlating means.

Further benefits and advantages of the invention will become apparent from a consideration of the following detailed description given with reference to the accompanying drawings, which specify and show preferred embodiments of the invention.

BRIEF DESCRIPTION OF THE DRAWINGS

The foregoing objects and advantages of the present invention for a contact lens production line pallet system may be more readily understood by one skilled in the art with reference being had to the following detailed description of several preferred embodiments thereof, taken in conjunction with the accompanying drawings wherein like elements are designated by identical reference numerals throughout the several views, and in which:

FIG. 1 is an organizational overview of the supervisory control system configuration of the instant invention.

FIG. 5(a) illustrates the data acquisition sequence for acquiring lens mold machine process data from either the front curve mold machine, back curve mold machine, or, primary packaging mold machine.

FIG. 5(b) shows the specific mold processing data items to be acquired from a front curve mold machine, back curve mold machine, or, primary packaging mold machine.

FIG. 7 illustrates one event block and one data block stored in PLC memory that are associated with PLC 11 shown in FIG. 20.

FIG. 11 illustrates the format of process records associated with particular pallet IDs that are sent to the relational database for long-term storage therein.

FIGS. 12(a)-12(b) illustrate the geometric orientation of the carrier pallets as they proceed from hydration through automatic lens inspection.

FIGS. 13(a) and 13(b) illustrate source memory queues for bar code scanners which contains pallet ID (index) information of pallets carrying lenses at the entrance to the hydration station.

FIGS. 21(a)-21(b) illustrate the sequence for creating a process parameter plot against a fixed time scale to illustrate process parameter trends in the system.

FIG. 22(a) illustrates a Pareto chart of alarm counts for the production line.

DESCRIPTION OF THE PREFERRED EMBODIMENT

As discussed in the co-pending patent application U.S. Ser. No. 08/257,790, entitled "Production Line Tracking and Quality Control System", assigned to the same assignee as the instant invention, the disclosure of which is incorporated by reference herein, there is described a contact lens manufacturing facility that is provided with a plurality of programmable and non-programmable control devices for controlling and monitoring various manufacturing processes in a contact lens manufacturing facility that produces contact lenses at a rate of 8 every 6 seconds.

Figure 20:
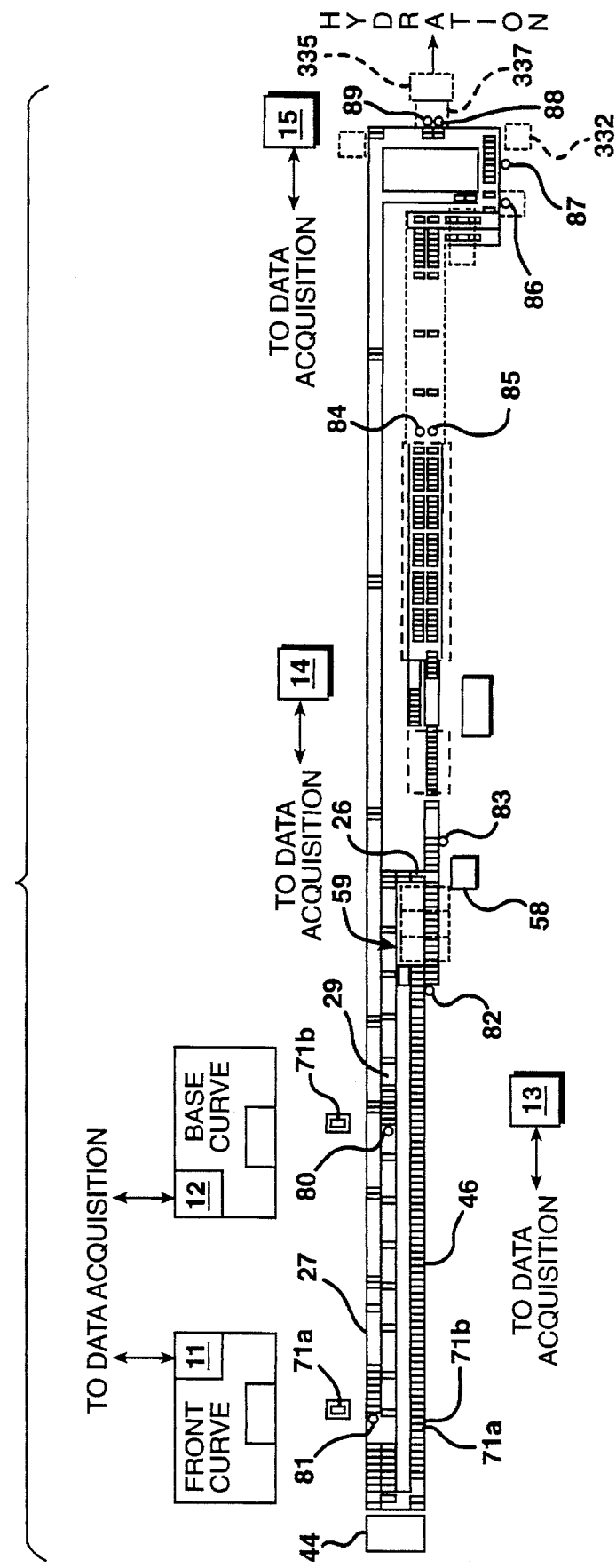
FIG. 20 illustrates a conceptual diagrammatic view of a pallet carrier and tracking system for a contact lens production line.

Particularly, there are two PLCs, indicated as 11 and 12 in FIGS. 1 and 20, for controlling the transfer of eight front curve (FC) and eight back curve (BC) injection mold halves from respective FC and BC injection mold machines (FIG. 20), to respective carrier pallets positioned adjacent first and second pallet conveyors, 27 and 29 respectively, both first and second pallet conveyors partially enclosed in a low-oxygen enclosure. The operational details are discussed in further detail in co-pending patent application U.S. Ser. No. 08/258,267 entitled "Apparatus for Removing and Transporting Articles from Molds", assigned to the same assignee as the instant invention, the disclosure of which is incorporated by reference herein.

As shown in FIGS. 1 and 20, a third PLC 13 controls monomer filling and contact lens mold assembly operations as discussed in detail in co-pending patent application U.S. Ser. No. 08/258,264entitled "Method and Apparatus for Contact Lens Mold Filling and Assembly", assigned to the same assignee as the instant invention, the disclosure of which is incorporated by reference herein. This PLC controls process conditions for monomer filling which consists of depositing, in a vacuum environment, a polymerizable compound (monomer mixture) for forming a contact lens in the concave portion of each FC lens mold portion in each carrier pallet 71a and, also controls the operation of assembling the individual contact lens mold assemblies which consists of picking each BC lens mold from pallet and placing them in an oriented configuration onto a corresponding associated FC lens mold carried by an adjacent carrier pallet 71a.

As shown in FIGS. 1 and 20, a fourth PLC 14 controls the precure, UV curing, and de-mold operations for the contact lens production line. This PLC operates to control the pre-cure process where the monomer solution contained in each mold assembly is partially cured into a viscous gel-like state and where the front and back curve lens molds are subject to a predetermined pressure to further define the contact lens edges, and, to eliminate decentration. The operational details for contact lens precure is discussed in greater detail in co-pending patent application U.S. Ser. No. 08/257,792 entitled "Mold Clamping and Precure of a Polymerizable Hydrogel" assigned to the same assignee as the instant invention, the disclosure of which is incorporated by reference herein. The operational details for contact lens UV curing is discussed in greater detail in co-pending patent application U.S. Ser. No. 0/257,799 entitled "Ultraviolet Cycling Oven for Polymerization of Contact Lenses" assigned to the same assignee as the instant invention, the disclosure of which is incorporated by reference herein. Generally, the fourth PLC also operates to control the polymerization process occurring in UV ovens where the precured lenses contained in the individual mold assemblies are formed into contact lens blanks. The operational details for contact lens de-mold operations is discussed in further detail in co-pending patent application U.S. Ser. No. 08/258,265 entitled "Mold Separation Apparatus" assigned to the same assignee as the instant invention, the disclosure of which is incorporated by reference herein. Generally, the back curve lens mold halves of the mold assemblies are automatically separated from the front curve lens mold halves to expose the polymerized contact lens for conveyance to the downstream hydration station.

As shown in FIGS. 1 and 20, a fifth PLC 15 controls the transfer of the front curve mold halves containing molded contact lenses to a hydration chamber where contact lenses are hydrated. This is explained in co-pending patent application U.S. Ser. No. 08/258,556 entitled "Automated Method and Apparatus for Hydrating Soft Contact Lenses" assigned to the same assignee as the instant invention, the disclosure of which is incorporated by reference herein.

A sixth PLC 16, as shown in FIG. 1, controls the post hydration operations as discussed in greater detail in co-pending patent application U.S. Ser. No. 08/257,796 entitled "Automated Apparatus and Method for Consolidating Products for Packaging", assigned to the same assignee as the instant invention, the disclosure of which is incorporated by reference herein. The post hydration operations include the generation of contact lens inspection data consisting of pass/fail results as determined by an automatic vision system of an automatic lens inspection station (not shown).

A seventh PLC 17 controls the primary packaging and lens package consolidation aspect of the lens packaging system as discussed in greater detail in co-pending pending patent application U.S. Ser. No. 08/257793 entitled "Interactive Control System for Packaging Control" assigned to the same assignee as the instant invention, the disclosure of which is incorporated by reference herein, and also controls processes such as solution exchange, saline fill, package foil heat seal, etc., which occur about a rotary index (packaging) dial as discussed in detail in co-pending patent application U.S. Ser. No. 08/257,787 entitled "Rotary Packaging Station" assigned to the same assignee as the instant invention and, the disclosure of which is incorporated by reference herein.

An eighth PLC (not shown) may additionally be provided for controlling various aspects of the secondary packaging including transfer of packages from the rotary index table to secondary package area and the subsequent sterilization of the packages at a sterilization station the details of which are described in co-pending patent application U.S. Ser. No. 08/257,788 entitled "Apparatus and Method for Sterilization and Secondary Packaging" assigned to the same assignee as the instant invention and, the disclosure of which is incorporated by reference herein. In the preferred embodiments, each PLC is a TI system 545 (Texas Instruments) and may include a TI 386/ATM coprocessor module for communicating with the respective PLC across the backplane or by serial link (not shown). It is understood that each PLC has its own memory and addressing capabilities for storing and updating blocks of data to be discussed in further detail below.

Other programmable device controllers are provided in a contact lens production line for controlling, respectively, the front curve mold machine 18a which produces the front curve lens molds at a rate of eight every six seconds, back curve mold machine 18b which produces the back curve lens molds, and, the primary packaging machine 19 for producing the contact lens packages in which the manufactured contact lens is contained. These programmable devices are manufactured by Yushin Corp.

Another device controller 20 controls a vision system that automatically inspects the contact lenses prior to their packaging. Operational details are discussed in greater detail in co-pending patent application U.S. Ser. No. 08/258,557 entitled "Automatic Lens Inspection System" assigned to the same assignee as the instant invention, the disclosure of which is incorporated by reference herein. Device controller 20 is manufactured by Perceptics based in Knoxville, Tenn.

As described in the above mentioned co-pending patent application "Production Line Tracking and Quality Control System", a production line pallet system provides high-speed transport of the back curve and front curve mold sections throughout various manufacturing stations of a contact lens manufacturing facility for manufacturing the contact lens. The production line itself is provided with a plurality of bar code scanning devices, indicated as elements 80–89 in FIG. 20, and mounted at strategic locations throughout the fabrication facility. Each bar code scanner device 80–89 is preferably a bar code laser scanner manufactured by Computer Identics Corporation Model No. Scanstar 110, located at Canton, Mass., and is provided for identifying each specific pallet or pallets carrying contact lens mold halves or mold assemblies. Specifically, each bar code scanner at the locations shown in FIG. 20, identifies each carrier pallet passing under it by scanning the pallet's unique identifying bar code (not shown). Each bar code scanner is provided with a decoding unit, such as Model No. Scanstar 240 (not shown), so that information in the form of a pallet identification number is input to each associated PLC memory locations depending upon the carrier pallet's location within the pallet system. Additionally, time stamp data, i.e., the time the pallet is scanned, is recorded by the PLC depending upon which bar code reader has made the scan.

Figure 12A:
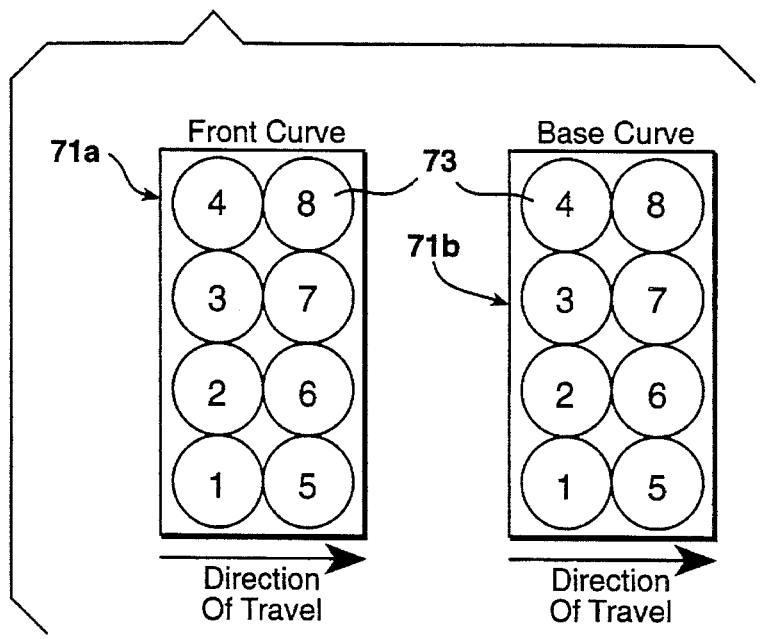
FIGS. 12(a)-12(b) illustrate the geometric orientation of the carrier pallets as they proceed from injection molding up to the hydration transfer.

The description of the above-mentioned carrier pallet for carrying up to eight contact lens mold assemblies may be found in co-pending patent application U.S. Ser. No. 08/257,786 entitled "Contact Lens Production Line Pallet System", assigned to the same assignee as the instant invention, and, the disclosure of which is incorporated by reference herein. FIG. 12(a) shows the conceptual layout for a carrier pallet 71a for carrying FC mold halves (not shown) or mold assemblies (not shown), and, carrier pallet 71b for carrying BC mold halves (not shown). Each pallet is interchangable in that it may carry either type of mold half. Additionally, shown in the FIG. 12(a) are the cavity positions 73 for retaining the individual FC mold halves, BC mold halves, or, mold assemblies on a carrier pallet. As will be explained in greater detail below, the cavity positions are numbered for tracking and time alignment purposes, i.e, for relating historical process control data generated and stored throughout the production process, with the vision inspection station contact lens pass/fail data of each lens produced in a pallet and specifically, with each cavity therein. As will be further described, a relational database is created that is used to store production records and long-term data histories. The supervisory controller system 10 provides for off-line access to this database and includes the mechanism for generating informative graphs including, but not limited to: scattergrams of process parameters vs. contact lens inspection results, histograms of defects by position on pallet, pareto chart of alarm count and duration by machine, time plot of cumulative inspection results, measured and calculated parameters plotted vs. time as a single trend, wherein trend fixed time scales are available to show data over minutes, hours, days, and weeks.

As shown in FIG. 1, the supervisory controller 10 of the instant invention monitors and analyzes performance for a contact lens production line. Referring to FIG. 1, there is shown the hardware elements of the supervisory controller 10, as well as the major software components that reside in each of the hardware elements. Essentially, the supervisory control system (control system) 10 includes five (5) types of processing nodes: a Data Acquisition Node 100 for communicating with each of the seven (7) programmable logic controllers (PLCs), discussed above, by means of communication lines 21a and TIWAY adapter card 21b, and also, for communicating with the device controllers of the three mold machines and the vision inspection machine by means of an 8-channel serial card 22, shown connecting the machines by dedicated asynchronous serial lines 23a,b,c,d, as shown in FIG. 1; a Relational Database Node 200 which runs relational database software 202 and includes at least three 200 megabyte hard disks provide for off-line data storage consisting of production records and long-term data histories; an Analysis and Routing Node 300 that contains most of the software that is used to initiate data gathering and processing of raw data from the seven PLCs, and, that maintains "real-time databases" that support statistical control charts and other displays; four identically-configured Operator Stations 400 that handle the presentation of graphs and displays for the operators of the production line; and, an Offline Analysis Node 500 that provides for analysis of data collected into the Relational Database Node after the data is no longer on-line, i.e. after a given run of the line. As shown in FIG. 1, ARCNET interface cards 101,201,301,401, and, 501 are provided for each respective nodes 100,200,300, 400,500 to support communication between the various nodes. An ARCNET network 99 supports communication among the seven processors mentioned previously.

Additionally, as shown in FIG. 1, standard workcell controller software modules provide additional functionality to the supervisor control system 10. The Alarms server 402 in operator Station 400 handles and maintains workcell alarms, warnings, and exceptions that are activated according to defined conditions. A Console Server 403 provides operator text-only presentation with input support to enable communication interface to all other administrators. The Display Server 404 provides data output using graphical emulation of workcell devices. The Graphs server 405 provides data output in the form of various type of graphs and charts on a computer graphics screen. This server supports the displaying and real-time updating of line, point, histogram, Pareto, x-bar-range, and other types of graphs and charts, and, also displays and updates graph overlays, such as straight lines and normal (Gaussian) curves typically used to portray computed statistical information about the data presented in a graph or chart. The Statistics Server 406 is the real-time database for the production line and stores data within logical user defined groups or datasets. It is capable of generating statistics and (optional) alarms on data sets. Each of the above-mentioned servers are standard CELLworks software that are commercially available software modules manufactured by FASTech Integration located in Lincoln, Mass.

Other software modules that reside in each hardware unit as shown in FIG. 1, include: A User Interface Manager 502 which is a module that coordinates the activities required to change screens on the Operator Stations 400. A Poller 505 which coordinates the acquisition of all data from the PLCs, Mold Machines, and the Vision Inspection Machine. A C-language Data Server 510 which takes blocks of information from PLCs, detects which data items in the blocks have changed, and sends the changed values to a Control Server 600. Event Server 503 is a C language server that takes blocks of event codes from PLCs, locates the correct alarm string for the event code, and forwards the string to the Alarm Server. The C-language Control Server 600 is a companion module to the Statistics server and directs the Statistics Server to perform statistical functions needed to support active displays. As the displays being viewed are changed, Control Server 600 issues new sets of commands to the Statistics Server. The C-language StatCount Server 506 keeps a running count of the frequency of different status codes (specified events) so that a Pareto diagram of status codes for a specific location (e.g., exit of de-molding station) may be rapidly displayed, and, a Type Server 508 converts numeric codes into text strings for display and also converts numeric codes into Boolean values to turn on and off colored graphics. In order to communicate with the Texas Instruments PLCs, a C-language ti_adm server 512 is provided for the link layer protocol handling associated with PLC communication.

The C-language Mold Servers 514a,b,c each receives message data from a respective Mold Machine 18a,18b, 19, and, extracts information from the message, and forwards all changed data to the Control Server 600. The C-language Vision Server 525 receives message data from the Vision inspection machine 20 and, extracts information from the message, and forwards all changed data to the Control Server 600. The C-language Alarm Control Server 528 keeps the Alarms Server in synchronization, keeps count of the frequency of alarm conditions and their duration in order to support Pareto diagrams of alarms, and automatically clears PLC alarms that the PLC reports as clear.

The functional descriptions of the hardware and software modules of the supervisory control system 10 of the instant invention will be discussed in greater detail below.

DATA ACQUISITION

As mentioned above, there are two types of input sources for the Supervisory Controller 10: the eight PLCs, and, the controllers for the Injection Molding and Vision Inspection Machines. The structure of event blocks and data blocks that the Supervisory Controller reads from each of the eight PLCs will be described. It should be understood that each PLC is automatically polled at least once every six seconds for data acquisition, however, the data is provided by each PLC to their respective event and data blocks, asynchronously. The supervisory control system 10 includes a processor clock (not shown) running at 33 MHz, that provides system timing for the polling function of the data acquisition node 100 and other control server functions.

Figure 2A:
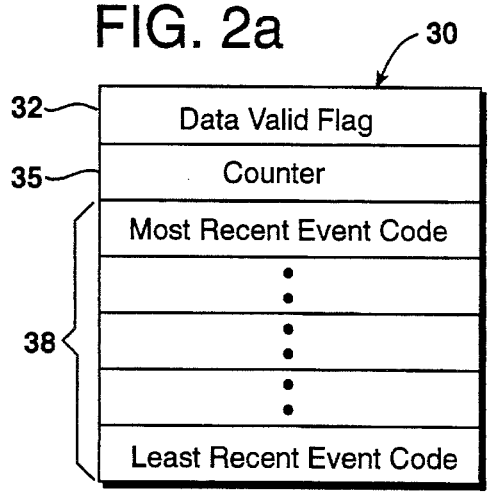
FIGS. 2(a) and 2(b) illustrate the memory layout for event and data blocks, respectively, that are generated by local PLCs and acquired by the data acquisition node of the instant invention.
Figure 2B:
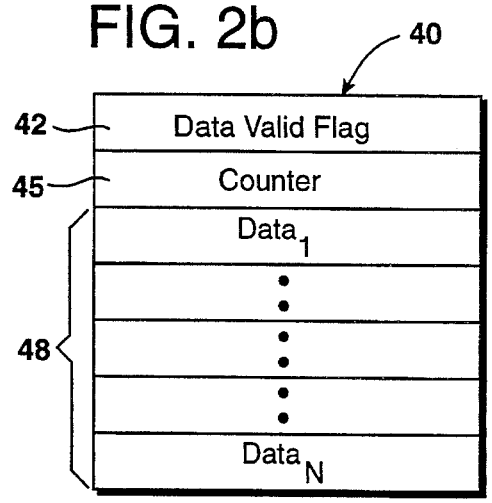

FIGS. 2(a) and 2(b) shows the structure of an event block 30 of data and a process data block 40 that is generated by the PLC from acquired data. Each event block 30 exists as a group of consecutive registers (memory locations) in each of the Texas Instruments PLCs. The Supervisory Controller polls the PLCs for event and datablock contents once every six seconds, preferably.

The first entry in the event block 30, is the data valid flag 32, which has a value of 1 when the block has consistent data in it. A value of 0 in the data valid flag indicates that the block was read from the PLC while the particular PLC was updating the block's contents. In this case the block will be read again.

The second entry in the event block 30 is a sequential counter 35 that is a sequential number that increases by one each time there are new readings. A change in the counter's value is used to inform the Supervisory Controller that the block has different information content, in addition to the number of new event codes in the block. The number of new event codes is added to the last value of the counter.

Finally, an array of event codes 38 is stored in the block. The most recent code event appears first, followed by the next most recent code, until the last entry is encountered, which is the least most recent event code.

In the data block 40, the first entry is the data valid flag 42 functions the same as that for the event blocks, described above.

The counter 45 in data block 40 is used to indicate that the data values in the block potentially contain new information and is a number that increases by one each time there are new readings. Following the counter is a block-specific sequence of data values 48; each value will be assigned to a different variable in the Supervisory Controller, as will be described in detail below. The counter can also be used to determine if the data for a process cycle was not read in a timely manner.

Figure 3A:
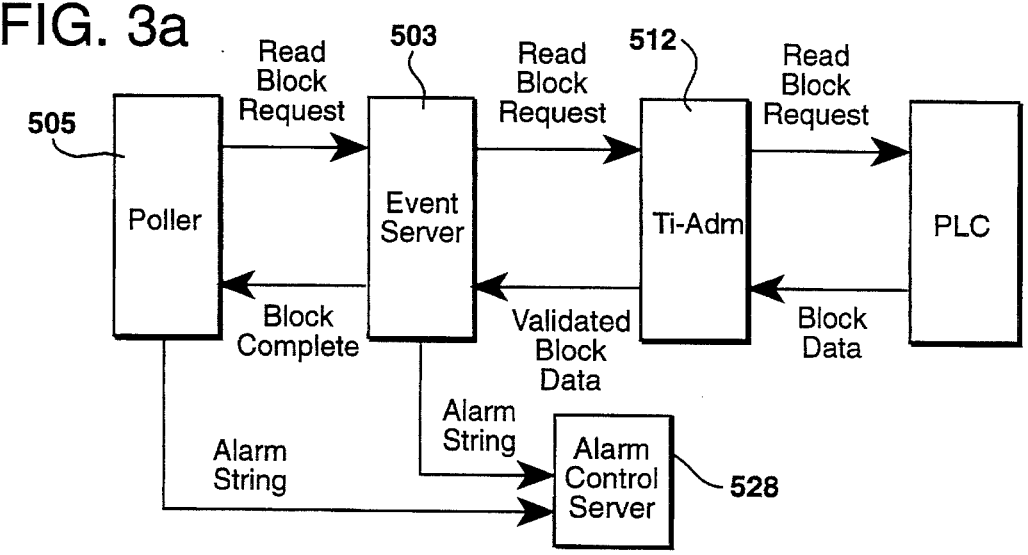
FIG. 3(a) illustrates the data acquisition process for acquiring blocks of event data from the local PLCs.

FIG. 3(a) illustrates the flow of PLC generated event block data through the Supervisory Controller 10.

Within the Poller 505, a list of the PLC-resident event blocks is processed one scan at a time, i.e., a request for each PLC 11–17 on the network is sent. Each block request is processed one at a time by the Event Server 503. The Event Server issues a read request for the block from the ti_adm 512, which communicates with the TIWAY interface card 216 and the PLCs that are connected to the TIWAY. Ti_adm 512 sends a "read block" request to the appropriate PLC so that the PLC may read the block from its memory. The PLC responds by sending the block to ti_adm via the TIWAY network. If the data valid flag 32 in the response is a 1, then the data is considered valid and sent to the Event Server 503. If the data valid flag is 0, ti_adm 512 will again request the PLC to re-read the event block. The ti adm then sends the validated block of data to the Event Server which then sends a "block complete" message to the poller informing it that the block was received successfully. The Event Server 503 then checks the counter 35 in the block 30 to see if it has changed from the counter value in the previous event block 30 (for that particular PLC). If it has changed, the difference between the previous and new counter values is the number of event codes in the new event block. For each of the new event codes, Event Server 503 sends the appropriate alarm string to the Alarm Server. As events are processed by the Event Server, a four digit code is formed by taking the three digit code sent by the PLC and appending it to a single letter code that identifies the PLC which the code came from. If there is a failure when reading an event block 30, an appropriate alarm is generated by the Poller. Both the event codes from the Event Server and failure codes from the Poller are sent to the Alarm Control Server 528.

Figure 3B:
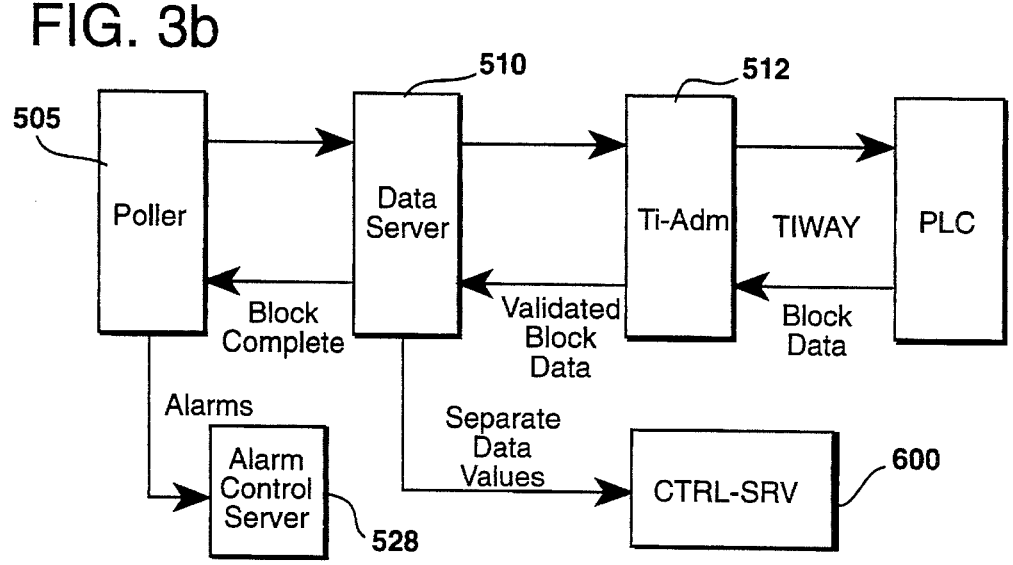
FIG. 3(b) illustrates the data acquisition process for acquiring blocks of process control data from the local PLCs.

The flow of PLC generated process data through the Supervisory Controller 10 is represented in FIG. 3(b) and is similar as described with the routing of event block data. Within the Poller 505, a list of PLC-resident data blocks 40 is processed one scan at a time, i.e. a request for each PLC 11–17 on the network is sent. An example of two blocks of information is shown in FIG. 7, which shows event block 78 and data block 79 that are stored in PLC memory for PLC 11 which controls the FC lens mold transfer to carrier pallet (FIG. 20). Each block request is processed one at a time by the Data Server 510. The Data Server 510 issues a block read request the block to ti_adm 512, which communicates with the TIWAY interface card 216 and the PLCs. Ti adm 512 sends a "read block" request to the appropriate PLC, and receives the PLC's response.

When Data Server 510 receives a block 40 from ti_adm, the data valid flag is read, and if it is a zero (0), the ti_adm will again request the PLC to re-read the data block from the memory. Additionally, the counter 45 in the block is inspected to see if it has changed from the counter value that was previously received for this block type. If the counter values are the same, no further processing takes place. If the counter values are different from the last reading, then each individual data item in the block is processed as follows:

Data Server 510 looks for and processes only changes in values for data items 48. Each data item in the block is checked against that item's previous value. If there is no change in the data item's value, Data Server moves on to process the next data item in the block. If the data item has changed from its previous value, then the data item is forwarded to Control Server (CTRL_SRV) 600 using a separate VALUE message for each data point. Note, that if there is a failure to read the data block, an alarm is generated and sent to Alarm Control Server 528.

The syntax for a VALUE message is shown as follows:

VALUE<sourcename><value> where sourcename is the name of the individual data point and value is the reading of the process parameter of measurement. An example of a value message indicating an $O_2$ concentration level of 0.0843% from an oxygen sensor is as follows:

ti VALUE CD/O2_LEV_$_2$84.3

Data server sends a COUNTER message to control server after all VALUE messages for a block have been sent. The COUNTER message is used to initiate processing of the block in the Control server.

The syntax for a COUNTER message is shown as follows:

COUNTER<countername><countervalue> where "countername" is the name of the counter, and "countervalue" is the value of the counter.

Figures 4A, 4B:
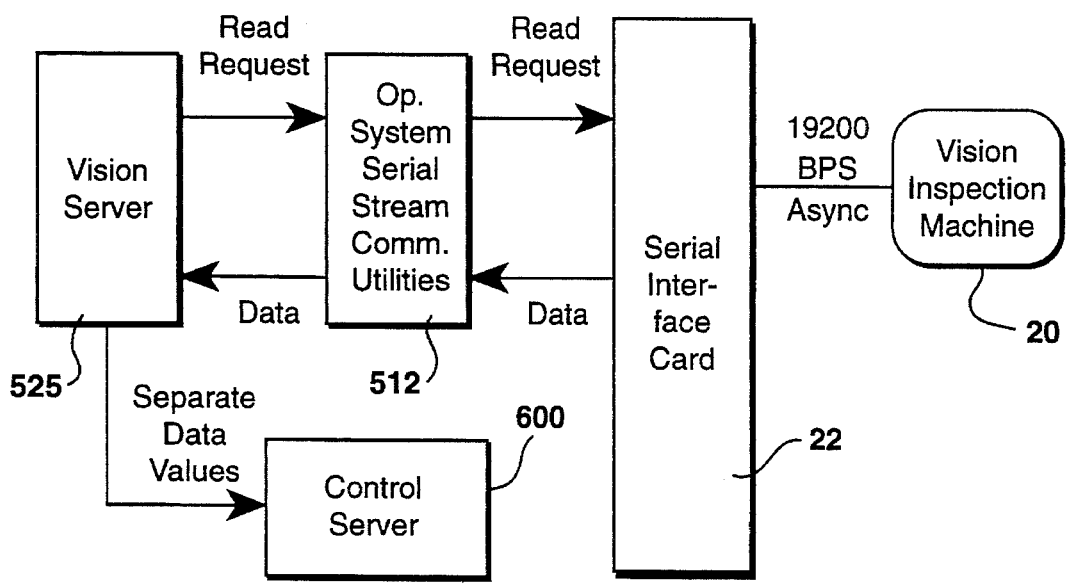
FIG. 4(a) illustrates the data acquisition process for acquiring lens inspection data from the vision inspection machine.
FIG. 4(b) shows the specific lens inspection data items to be acquired from the vision inspection machine.

Data that is sent by each of the Mold and Vision machines does not have the block format of the data coming from the PLCs, and, the injection mold and vision controllers are not polled. Instead, the Mold and Vision controllers send the Supervisory Controller messages that are actually text streams and which are sent when the respective machine has the information. In FIGS. 4(a) and 5(a), the process of obtaining data from these respective machines is shown.

For the vision and mold machines, as shown in FIG. 4(a) and 5(a), respectively, the Vision server 525 (and each mold server 514a,b,c) use the operating system communication utilities to issue a read request. This is done only once during system startup. The operating system communication utilities then sends a read request to the serial interface card 22 which is connected with the respective mold and vision machines. For the vision inspection machine 20, after each vision inspection cycle, the machine sends inspection data to the supervisory controller through the serial interface. The data is sent in a series of ASCII messages, one message per lens. The messages are intercepted by the operating system's communication utilities software. The Vision Server 525 parses each message, decomposes the message by extracting nine data items from the message, and forwards the nine data items to the control server 600 using the VALUE and COUNTER messages. A counter value is also reported to the control server every group of eight (8) lenses so that the Control Server can do block processing.

As explained in greater detail in the abovementioned co-pending patent application U.S. Ser. No. 08/258,557 entitled "Automatic Lens Inspection System", the vision inspection reports results for each lens inspected which comprises a data stream 50, as shown in FIG. 4(b). The data stream includes an entry 51 for the specific lens number (1–16) on the lens inspection pallet, the pass/fail entry 52 for that lens, the inner flaws and inner score results 53 and the outer flaws and outer score 54, the combination defects and combination score 55, the total score 56 for the lens, and the center lens inspection code 57. This data will be stored in a group of data samples discussed below and associated with a particular pallet for long-term storage in the relational database.

Likewise, after each mold injection cycle, each mold machine sends process data to the supervisory controller through the serial interface. The data is sent in a series of ASCII messages, one message per pallet of lens molds. The messages are intercepted by the operating system's communication utilities software. Each individual Mold Server parses each message, decomposes the message by extracting fourteen data items from the message, and forwards thirteen of these data items to the control server 600 using the VALUE and COUNTER messages.

The typical data items for the mold controller machines are illustrated in FIG. 5(b) and comprises a data stream 60 having about thirteen entries including: an entry 61 for timestamp information, which is not sent to the control server 600, an entry 62 which is a locally generated count of the number of lens molds produced, and, includes other mold controller processing conditions including cycle time (entry 63), plasticizing time (entry 64), filling time (entry 65), injection mold peak pressure (entry 66), injection mold temperatures (entries 67 and 68), etc. Again, each mold server 514 identifies each data item with a unique name when it is sent to the control server.

As will be explained in detail below, after the Control Server receives VALUE messages, they are processed further and correlated with a particular index, i.e., the pallet number, and timestamp, so that historical records of process control data may be archived in a relational database along with lens inspection results and records of events. Process parameters applied to each pallet as they pass through the line are also archived in the permanent database, as mentioned above, and each inspected lens record is referenced back to its parent pallet.

CONTROL SERVER

The functional objectives of Control Server are to: route source data messages to the STATISTIC Server 406; to provide dynamic setup data to STATISTIC Server so that it supports the data needs of user interface screens (not shown) as they change; and, to collect data into workflow records and forward the records to the relational database 202 for archiving.

Figure 6:
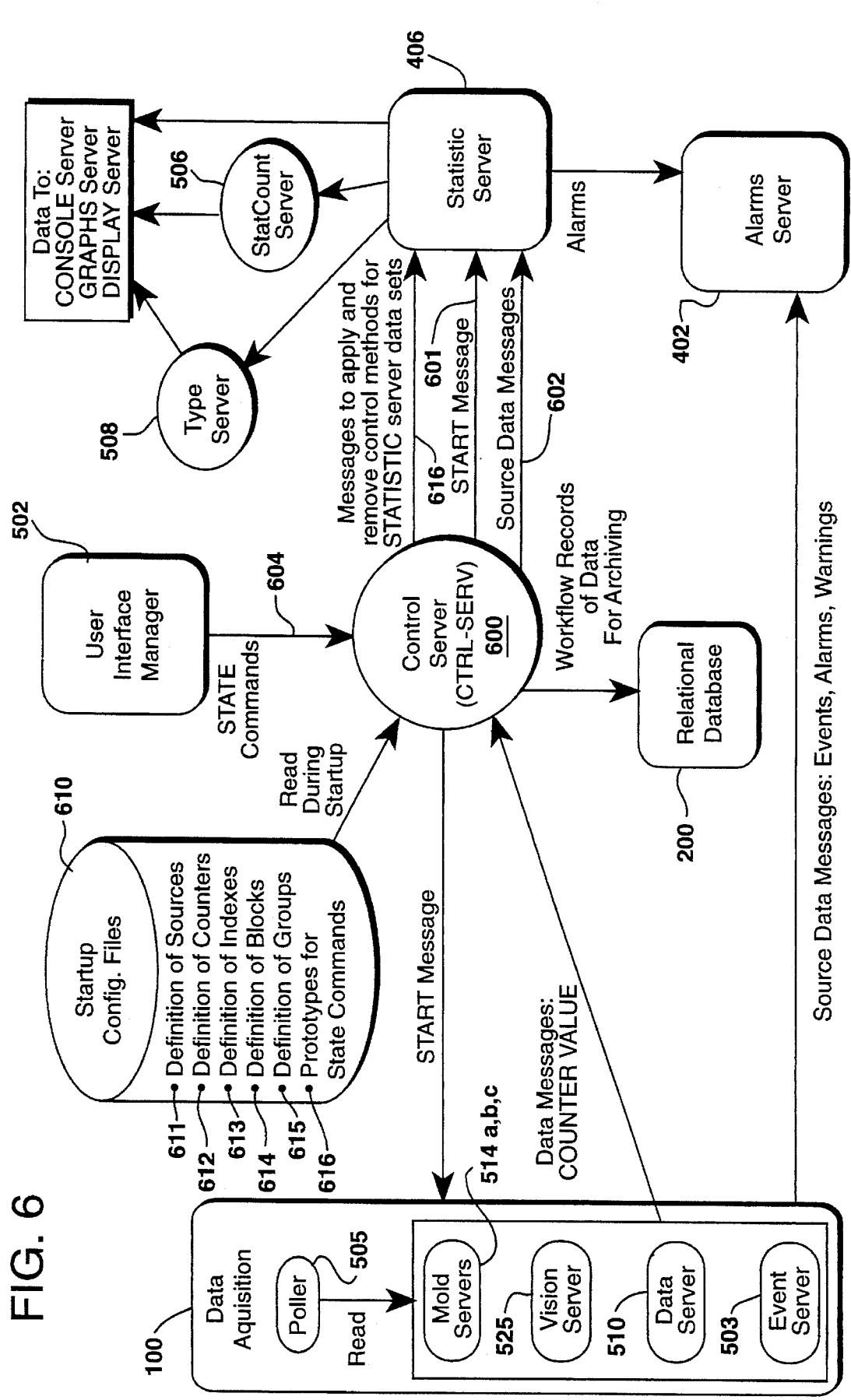
FIG. 6 is a diagram showing the functional relationships between the Control Server and other modules of the Supervisory Controller.

FIG. 6 is a diagram showing the functional relationships between the Control Server 600 and other modules of the Supervisory Controller 10.

At system start-up, Control Server 600 reads and processes startup configuration files 610 ("include files") that describe the organization of the process data the Control Server will work with. Data sources 611, counters 612, indexes 613, blocks 614, and groups 615, are defined in the configuration files. Each of these entities will be discussed in further detail below. Also included in the startup configuration files are prototypes for sequences of commands (templates) 616 to be sent to the STATISTIC Server 406. The prototypes 616 are used during run-time to describe the operations statistic Server 406 must perform on data sets in order to support active displays. The operations, for example, could include direction to calculate a mean and standard deviation for a specific data set. The prototypes 616 would also contain data "sink" information for STATISTIC Server, i.e., where to send the information that it produces. Additionally, the Control Server receives from the configuration files the commands that define process limits and the messages that the Statistics server should send to Alarm Control Server when limits are violated.

Control Server 600 also directs the startup of the STATISTIC Server modules when Control Server is ready to operate. A START command 601 is issued to STATISTIC Server, and Control Server waits for it to be ready before beginning real-time operation.

DATA POINTS

As mentioned above, the Control Server receives process data from the three Mold Servers 514a,b,c, the Vision Server 525 and the Data Server 510. The points are not received as point aggregates, but are received one point at a time as VALUE messages described above. Only data points that have changed are given to Control Server to ensure that system resources are not expended in repeating point values that are static. The Control Server 600 takes each new data point value and saves it in a local memory location or queue for the "most recent" value for that point. In the contact lens manufacturing system, there are approximately four hundred data points for input to the controller. Data points are defined to the control server as sources, and, at system start-up, will receive SOURCE commands 611, the syntax of which is as follows:

SOURce<source>[Type=<datatype>][ID=<id>][Cycle=<msec>] [Units=<label>][±Dataset]

The following example specifies the label and other characteristics for a data acquisition sensor, contact, or machine fault.

Example:
 source SEQ_CNT

The optional "Type" argument of the SOURCE command is a two character string defining the type of data to expect:

AI synchronous analog input, real number data;

DI synchronous digital input; 1 or 0,

CI asynchronous contact input; SET or CLEAR'ed with optional value

EV asynchronous event; optional value.

The optional argument "ID" is a four character string that is used as a cross-reference for other labeling schemes. The optional "Cycle" argument is the cycle time is milliseconds, where cycle time includes the duty time and the return time. The optional argument "Units" is a ten character string for storing the engineering units. With DI points the units are used as the data attribute forwarded to STATISTICS Server when the point value is 1. If the "–Dataset" flag is specified, updates will not be sent to STATISTICS Server. The "+Dataset" flag re-enables forwarding, which is the default for any new source.

BLOCKS

Blocks are collections of data points (data sources). Control Server blocks are aligned with the definitions of blocks as the PLCs and Data Acquisition understand them. By defining a block, the user is telling Control Server that a set of points is updated in the PLC as a unit, and the set is transmitted from the PLC to the Supervisory Controller 10 as a unit. Each block known to Control Server has a data point defined that is a block trigger and defined to Control Server as a COUNTER. The trigger is a source that is reported to Control Server after all the other points in the block have been reported. When a new value is received for the trigger, Control Server takes two actions:

1) All of the data points that can be sent to STATISTIC Server (the points that have not been flagged with –Dataset) that are part of the block are sent (one at a time) to STATISTIC Server. Since the trigger is the last item in a block to be sent from Data Acquisition to Control Server, all the data points in the block are current when the block's contents are shipped to STATISTIC Server. Note that Control Server sends all the block's points to STATISTIC Server whether or not the points have changed from their previous readings.

2) The history for each data point (source) is updated in the memory queue allocated to the specific process, if required. Successive values for any data point may be stored in memory queues so that there is a history of the "N" most recent samples for a point available. The usefulness of doing this will be evident when samples are discussed below.

In summary, block triggers are the mechanisms that 1) cause process values to be sent from Control Server 600 to STATISTIC Server 406, and, 2) bring about data point source history updates.

Blocks are defined to the Control Server by means of the BLOCK command, the syntax of which is as follows:

BLOck<block>Counter=<source>[<source>]

The following examples specify a set of sources whose values change in synch with a machine cycle counter.
Examples:
block LFBC c=BC_L_CNT 02TIMEBC ID_02_BC
block LFBC 02TIMEFC ID_02_FC
Every source that feeds the STATISTICS Server dataset must be part of a block. The "Counter" argument is a source that should be reported after all the block's sources have been updated for the current cycle. If a source is not updated, it is assumed to keep its previous value. Counters are used as triggers for samples and groups for creating a relational database memory record as will be explained in further detail below. A block definition can be modified to include additional sources by repeating the block without a counter.

SAMPLES

For the Supervisory Controller, there is a requirement to collect and save process information that is pertinent to specific pallets of lenses as they move through the process. The Control Server 600 permits time-aligned data to be collected and saved.

A sample is a collection of source data (data points) that can be bound to either a pallet ID or to a counter. The typical use in the Supervisory Controller is a collection that is bound to a pallet ID. Since bar code readers are not located at every point in the process where a measurement is taken, the Control Server 600 provides a way to time-align the data with the pallet ID from the bar code reader.

Time-alignment of source data with pallet IDs can actually take place in one of two ways. Both techniques may be used in the system at the same time for different sample definitions.

1) If the bar code reader is downstream of the sensors for the source data, data point information relating to a specific pallet must be saved for a while until the pallet passes the bar code reader. The sample will be triggered by receipt of a block trigger. When Control Server receives the bar code (the pallet ID), the process data that has been temporarily stored can be retrieved and associated with the pallet ID. For example, as shown in FIG. 20, bar code reader 82 is located downstream of the pallets that are subject to a degassing process in the nitrogen enclosure 46. Therefore, when pallets 71a,71b are exiting the tunnel 46 and are identified by bar code scanner 82, then the sample created by a block trigger will be associated with a specific pallet (index).

2) For the case in which the bar code reader is upstream of the sensors for source data, the bar code readings are saved and matched with data points at a later time. For this case, receipt of a block trigger can be used to gather the source data defined for a sample. An important example is how the lens inspection results are correlated to a bar code pallet ID. As shown in FIG. 12(*b*), the pallet IDs of pallets 71a,71c that passes respective bar code readers 88,89 are stored in source memory queues 660,660', respectively, as shown in respective FIGS. 13(*a*) and 13(*b*), and data that is subsequently generated from the vision inspection machines will be associated with a specific pallet ID index that is retrieved from these source memory queues. This is because there is a predetermined amount of machine cycles from the time that a pallet ID bar code is scanned to the time that the lenses from that pallet ID are inspected at the ALI station. Thus, as will be explained in further detail below, a sample command will be defined such that, when triggered by a counter from the vision inspection machine, vision inspection results for a specific pallet will form a sample with the correct pallet ID located at a prespecified memory offset in the source memory queue for the bar code readers 88 or 89.

When a sample is defined (using the SAMPLE command), the source data that goes into the sample is defined along with an offset for each source item. The offset tells Control Server how many cycles back in the source's history to go to get the value that belongs in this sample. For example, a zero offset tells Control Server to get the current source value, and an offset of one means that the source value one cycle ago should be collected.

Every sample has an associated index that distinguishes it from other samples taken under the same sample definition. The bar code value is typically used for the index. The syntax for the SAMPLE command is as follows:

SAMple<sample>Trigger=<counter>[Index=<source>Offset=<delay>][Source=<source>Offset=<delay>]

The following examples specify an ordered set of source values to be captured and formatted in a database record.
Examples:
    sample NUTIME tri=F_A_CNT i=DEPB_ID o=0
        s=NUTIMEAB o=0
    sample NUTIME s=NUTIMEAB o=0

Specifies an ordered set of source values. The "Trigger" argument is a block whose counter initiates capture for eventual storage in the database. The optional "Index" argument is the source that contains the barcode for the record where the sample is placed. The optional "Offset" argument is used to access a barcode that was read in a previous cycle. If the index source is not specified then the current value of the trigger block counter is used. Each source value for the sample is accessed with its own offset. Offsets are not used to reference values in future cycles. A sample definition can be modified to include additional sources by repeating the sample without a trigger and index.

GROUPS

Figure 8:
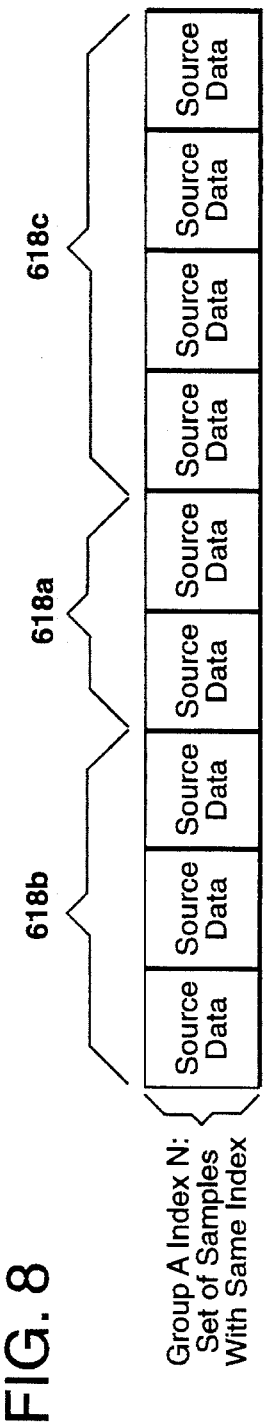
FIG. 8 is a simplified diagram illustrating the interrelationship between source data points, samples, and groups.

When a set of samples is collected with the samples having the same index (same pallet ID), a group is formed that is a workflow record of the process conditions that affected the pallet as it moved through the line. FIG. 8 illustrates how source data points, samples and groups having the same index are related to one another. Samples labelled 618a,b,c correspond to blocks of 2, 3, and 4 source data points, respectively. Thus, in FIG. 8, sample 618b, is composed of three source data points which will be accumulated at each process cycle, as will be explained in further detail below.

When a pallet has completed its journey through the process, all of the samples for a group will be collected and the group will be complete. In terms of the illustration in FIG. 8, the group for an index is complete when all of the samples in the group's row have been taken. A group for a specific index (bar code) must be ended and flushed to the database at every diversion point as a particular pallet may be diverted (rejected in the system) and not seen again by a bar code scanner. Therefore, there will be several groups with different sample definitions (and different names) that will correspond to different portions of the line, but will have the same index (pallet ID) number.

When a group is complete, the information in the group is sent to the relational database for long-term storage. Groups are defined to the Control Server using the GROUP command, the syntax of which is as follows:

GROup<group><maxrec>Trigger=<block>

[Index=<source>Offset=<delay>] [REFindex=<index>]
[Test=<source>Offset=<delay>[Clear=<group>] ]
[Label=<label>] [<sample>]

The following examples specify an ordered set of samples for a database record.
Examples:
    group AB 256 tri=SERVO_CNT i=BCR3_IDB o=0
        l=pallet NUTIME NUBUFB FAENCB MONOB
    group AB CHM1B CHM2B CHM3B CHM4B DEPSB The "Trigger" argument is a block whose counter initiates sending of the record to the relational database and may be the same argument as that for forming the sample. The optional "Index" argument is the source that contains the barcode for the record that should be sent. The optional "Offset" argument is used to access a barcode that was read in a previous cycle. If no offset is given, the current value of the trigger block counter is used. A group definition can be modified to include additional samples by repeating the group without a trigger, index, and test source. The optional "Test" argument is used to control whether the indexed record is transmitted. The record is sent if the test source at the given offset has a non-zero value when the group is triggered. As will be explained in detail below, the formatted message that is sent to the relational database starts with a tag specified by the optional "Label" argument.

Figure 9:
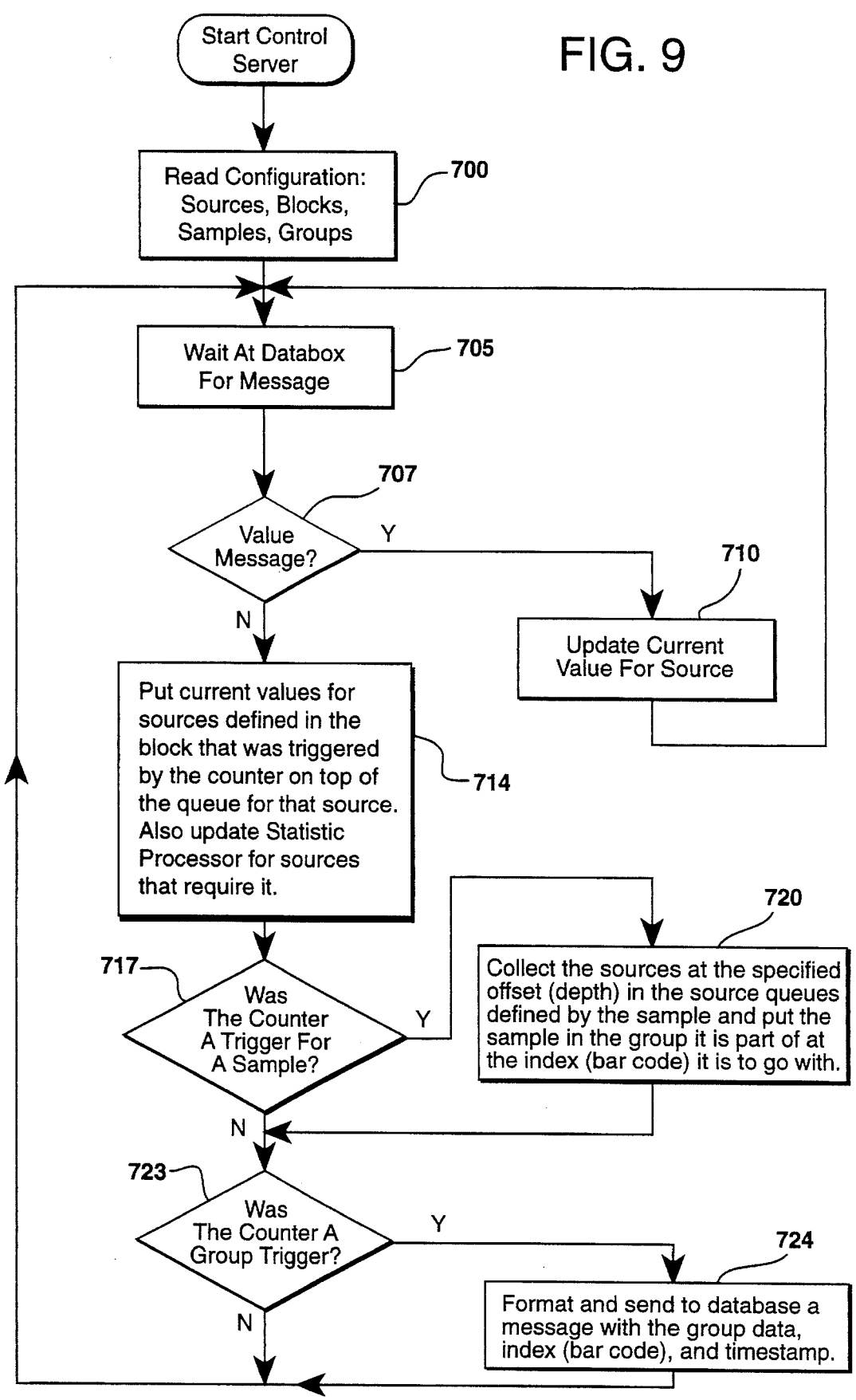
FIG. 9 is a logic flow diagram illustrating the function of the Control Server for generating database records.

As illustrated in the logic flow diagram of FIG. 9 setting forth the steps for creating a database record to be sent to the relational database, Control Server 600 first reads and processes startup configuration files at step 700 as discussed above. Then, at step 705, the control server will wait for a message to appear in its data mailbox location (not shown). The mailbox is part of a messaging service (MBX) that is supported by the Arcnet network, that lets processes (tasks) in the system exchange information with each other, even if they are running on different computers. Thus, each process will wait for a message to be written to its mailbox location so that the message may be retrieved and forwarded to the specific task in the same order in which they are written to the mailbox (a FIFO type of queue). In this case, the VALue message is sent from data acquisition and input to the data mailbox for retrieval by the Control Server. At step 707, the control server makes a determination as to whether the message is a value message. If so, the current value for the source is updated at step 710.

Figure 10B:
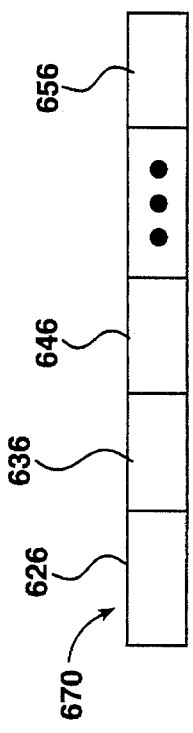
FIG. 10(b) illustrates a typical sample comprising data points taken from the memory source queues at prespecified offsets.
Figure 10C:
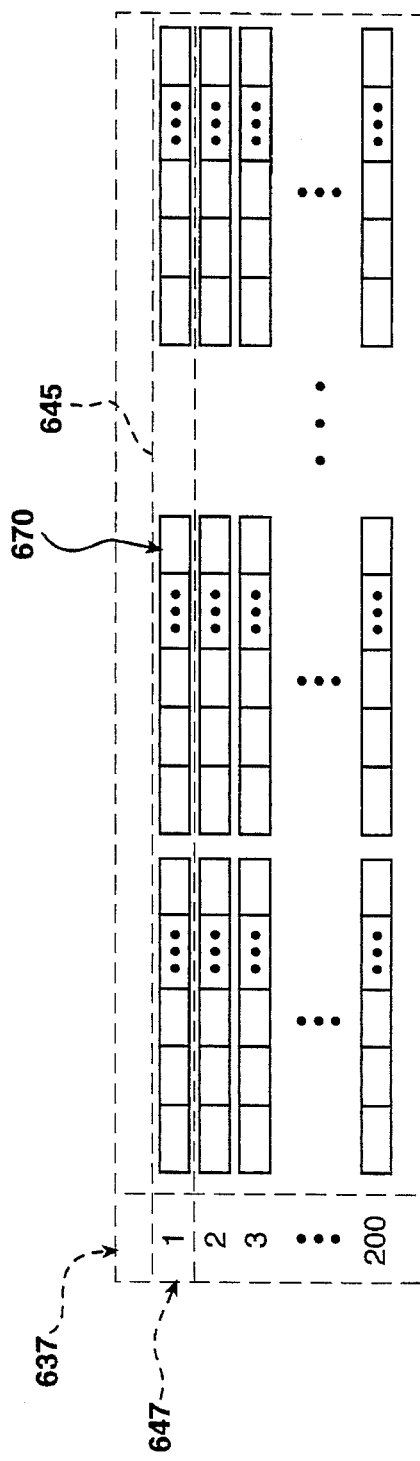
FIG. 10(c) illustrates the concept of samples that are collected to form a group with an associated index.
Figure 10A:
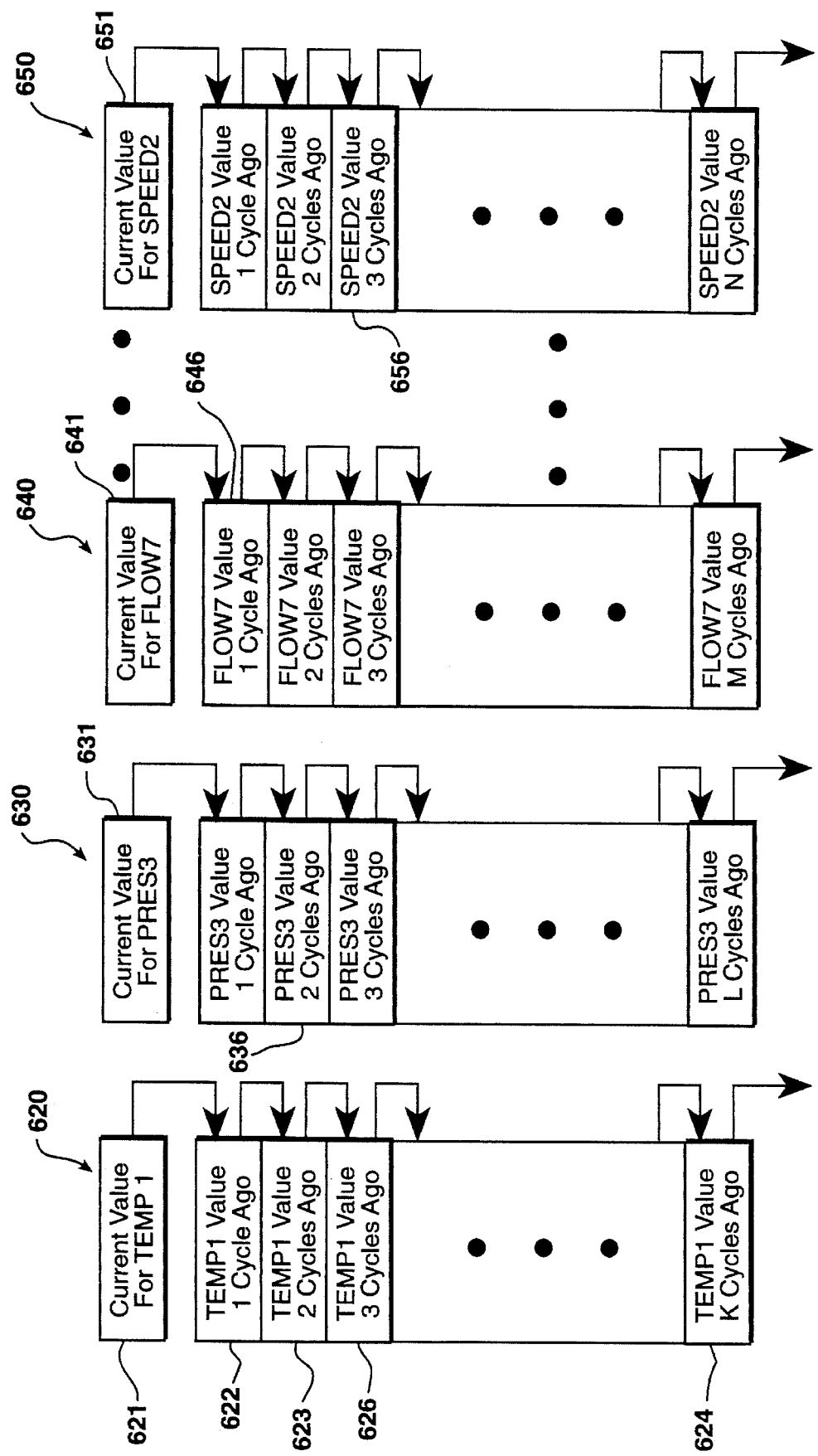
FIG. 10(a) illustrates a series of memory source queues within control server memory for storing a history of data points for particular processes.

FIG. 10(a) illustrates a series of memory source queues 620, 630, 640, and 650 for storing a history of data points. When a value message is received as determined at step 707, the data contained therein is updated stored in a current memory location associated with each respective source queue. For instance, memory locations indicated as 621, 631, 641, 651 will store the current values for data points related to a temperature process parameter, pressure, flow, and conveyor speed process parameters, respectively, when they are first received.

If the message received is not a value message as determined at step 707, then it is a counter message as discussed above. The control server then acts to place the current data values for each source defined in the block that was triggered by the counter on top of the memory queue for that source, as indicated at step 714. By doing this, all values are shifted, as shown by arrows in FIG. 10(a), so that a time alignment of the data values may be maintained. For example, upon receipt of the counter trigger, the current value for Temp 1 in location 621 of source queue 620 is input to memory location 622 which is the memory queue location for storing the Temp 1 value (data) of the preceding machine cycle (one machine cycle ago). The Temp 1 value that was in location 622 will now become the temp 1 value of two machine cycles previous, as indicated at memory location 623 in FIG. 10(a). This is repeated for each location of the memory queue. The Temp 1 data value of K cycles ago as shown in queue location 624 will be discarded. As can be seen in the FIG. 10(a), the length of each memory queue 620, 630, etc. for storing the history of specific process parameter is process dependent. Thus, up to "K" Temp 1 process readings will be kept in queue 620 corresponding to the values obtained for each machine cycle up to K cycles ago, and, up to "L" PRES3 data readings will be stored in queue 630 corresponding to the values obtained for each machine cycle up to L cycles ago. It should be stressed that each bar code scanner in FIG. 20 has associated with it a source memory queue such as the memory queues described above. The data contained in the memory queue for a specific bar code represents the pallet ID bar code numbers for each pallet that passes under that bar code scanner.

At step 717 in FIG. 9, a determination is made as to whether the counter trigger received by the specific block is also defined as a trigger for a sample. As discussed above, if the trigger to form a sample is received, as indicated at step 720 in FIG. 9, all the source data specified by the sample command will be collected from their respective source queues and a sample of the data values will be stored and collected within a group to be indexed with an associated bar code as explained in further detail below. As described above with reference to the sample configuration command, data from the source queues may be collected at any specified offset (depth) as predetermined. Thus, as shown in FIG. 10(b), a sample collection command may specify source queues 620, 630, 640, and 650 and offsets 626, 636, 646, and 656 to form a sample 670, that contains time-aligned process data associated with an index.

As illustrated in FIG. 9 at step 723, a determination is also made as to whether the counter trigger received from the specific block is also functioning as a trigger for a group. As discussed above, when the appropriate trigger is received samples with the common pallet ID number are gathered to form a group. The group command defines the samples contained in the group, and also defines the trigger that results in the group being sent to the database.

FIG. 10(c) illustrates the concept of samples that form a group. The column 637 contain the unique bar code numbers (index) for every pallet contained in the system. It should be understood that the column of bar code pallet ID numbers are not necessarily in any numerical order and can be random. Each row 647 in FIG. 10(c), represents the group containing the samples for the specific pallet ID identified in the column. As shown in the FIG. 10(c), for e.g., the group 645 includes sample 670 described previously.

At step 724 in FIG. 9, the formation of the database record containing the group data and barcode index will be sent to the relational database. At the time the record is sent to database, it is timestamped by the control server to function as an additional index for a specific group of data. If the group trigger was not received in step 724, then the process is repeated and the control server waits for the next message at step 705.

The time-stamp information (index) may be used to identify product processes occurring during specific periods where conditions external to the automated contact lens system (i.e. air conditioning, humidity, "clean room" conditions, etc., may have effected product quality.

FIG. 11 illustrates the format of groups of records labelled 1,2, . . . ,n, that are sent to and stored in the relational database 202 (FIG. 1). As shown in FIG. 11, the column 657a contains the date and timestamp information of the individual transmitted record as generated by the control server. Column 657b contains the bar code index (pallet ID) number. Column 657c contains the label information, which, in the preferred embodiment, is a combination of the group name and a coded date/time that control server sends to the database for a specific record. The remainder of the columns 657d contain up to "J" source data values containing the history of the particular processing occurring at a specified part of the contact lens fabrication facility. It should be understood that another record having the similar structure to records 1,2, . . . ,n, shown in FIG. 11, may have the same pallet ID number but may represent processing in the same part of the contact lens fabrication system but at a different date and time, or, may represent that the processing had taken place for the same pallet but at a different part of the system, for e.g., after pallet rejection at the exit of the mold assembly station, or, at ALI vision inspection processing. It should be understood that for the case where more than one record is created for the same pallet index, there may be fewer or greater data source values within each record, depending upon where in the production line the processing had occurred.

Vision Inspection Results

As illustrated in FIG. 20 and discussed in further detail in above-mentioned, co-pending patent application U.S. Ser. No. 08/257,786, following injection molding of and deposition of back curve and front mold halves on respective back and front curve carrier pallets, and after entry into a nitrogen buffer tunnel 46, a double cross-pushing mechanism 44 pairs a pallet containing front curves with a pallet containing back curves for conveyance to a filling and mold assembly station 59. At filling and mold assembly, the front curve mold halves are dosed with monomer and the back curve carrier pallet and placed on top of the front curve molds that contain monomer. The back curve pallet is subsequently re-routed back to the injection mold station for re-use. If, an alarm condition exists and it is determined that the lenses carried by a particular pallet is flawed and should be rejected as further described in above-mentioned co-pending patent application U.S. Ser. No. 08/257,790 entitled "Production Line Tracking and Quality Control System", then a ram pusher apparatus 58 shown generally in FIG. 20, will be commanded to reject the particular pallet containing the flawed lenses as well as recirculate the empty back curve carrying pallets exiting the filling and mold assembly station 59 from conveyor 26 to conveyor 29.

FIG. 12(a) illustrates the orientation and direction of travel of the front and back curve pallets 71a,71b, respectively, just prior to entering the filling and mold assembly station. As seen in FIG. 12(a), the cavities of each pallet are numbered 1,2, . . . ,8 in a specific orientation.

Figure 12B:
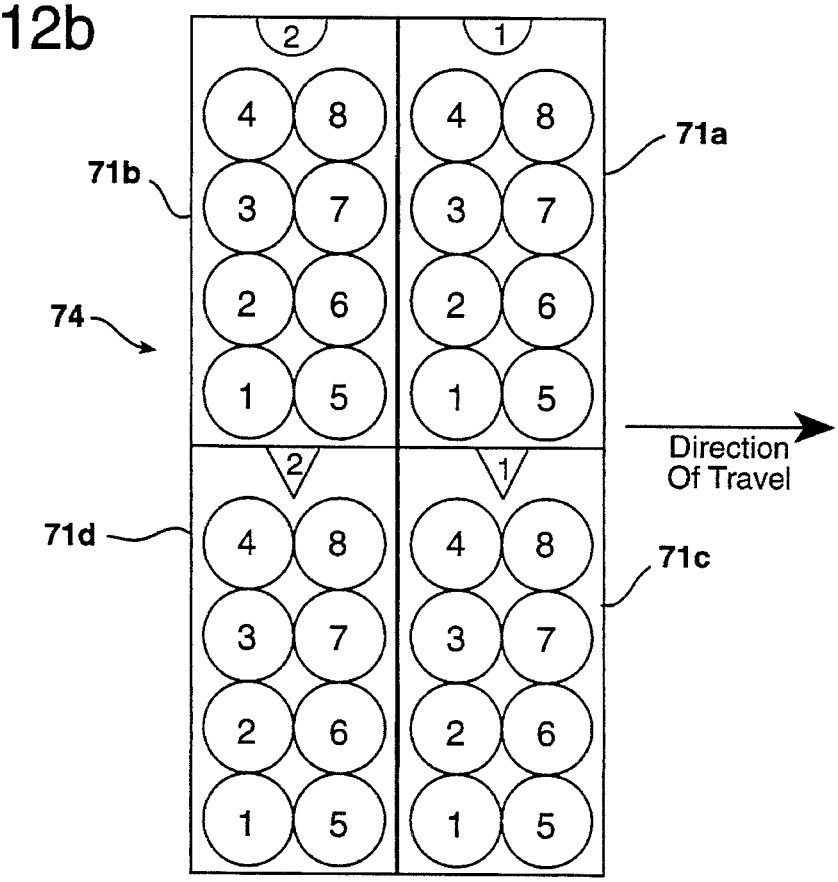
Figure 12C:
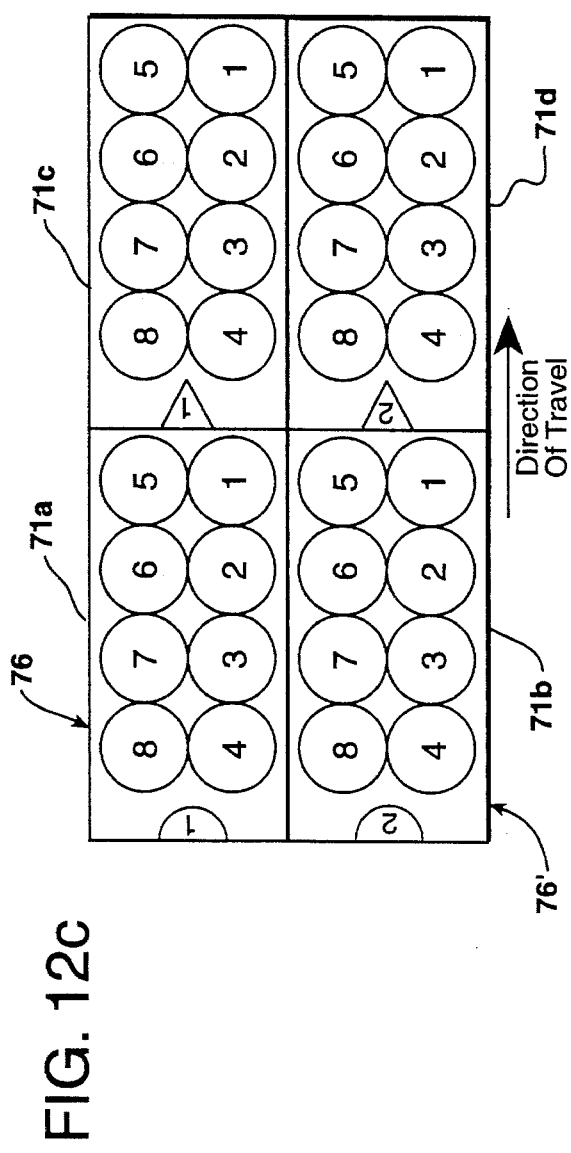

After exiting the mold separation apparatus and prior to entering hydration chamber 335, as shown in FIG. 20, the pallets containing completed contact lenses are paired so that two pallets are moving side-by-side. At the hydration station, pusher apparatus 332, is timed to enable the staging of four (4) pallets 74 on a carrier 337, enabling thirty-two (32) contact lenses to be grouped for hydration processing. FIGS. 12(b) and 20 illustrate the orientation of each of the four pallets 71a,b,c,d when staged on carrier 337 for conveyance to the hydration station. As shown in FIG. 20, bar code scanners 88 and 89 identify each of the pallets before they are transferred to hydration. Specifically, bar code scanner 88 reads bar codes of pallets labelled 71a and 71b in FIG. 12(b) and bar code scanner 89 reads bar codes of pallets labelled 71c and 71d. This is the last bar code reading in the contact lens production process. Since the lenses themselves are removed from the pallets, and, since there are no further bar code scanners from this point, lens location and identification during hydration and post-hydration is inferred from machine cycle counts. As briefly mentioned above, a source memory queue is created for each bar code scanner and the data contained in each bar code scanner memory queue comprises the pallet ID numbers that pass under it. FIGS. 13(a) and 13(b) illustrate bar code memory queues 660 and 660' respectively, that correspond to bar code scanners 88 and 89 (FIG. 20) and that retain pallet ID data (index) values therein. When a pallet passes under bar code scanner 88, for example, the pallet ID data is placed in location 661, i.e., the location where the current data is stored. As subsequent pallets pass under it, the original pallet ID data and all pallet ID data that is collected thereafter, is shifted within the memory queue one memory location at a time, as indicated by the broken arrows in FIG. 13(*a*). Then, when a sample is triggered for gathering vision inspection source data (results), a specific offset for the source bar code scanner 88, for instance, the pallet ID index located at memory queue location 662 will be grouped with the lens inspection result data. This sample is triggered upon receipt of the counter from the vision server, and the amount of offset is predetermined as programmed in the configuration file sample definitions read by the control server at system startup.

At the exit of the hydration station the lenses undergo a 90° counter-clockwise rotation as they are picked and placed in injection molded blisters (not shown) that form the bottom part of the lens packaging and that are carried in inspection carrier pallets 76 and 76' that carry sixteen (16) injection molded blister packages as shown in FIG. 12(*c*). FIG. 12(*c*) illustrates the orientation of sixteen packages each in inspection pallets 76 and 76' as they are conveyed up through post-hydration. Each lens position on the inspection pallets 76, 76' is shown illustrated and compared with their cavity locations in the original pallets 71*a,b,c,d*.

Figure 12D:
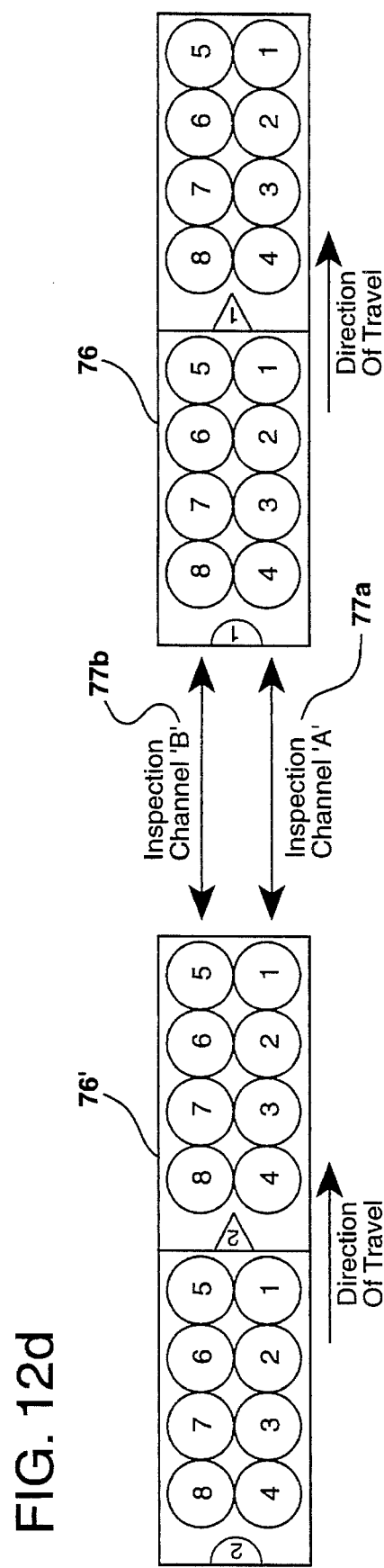

Prior to entering the ALI vision inspection station, the packages are engaged in a predetermined manner. FIG. 12(d) illustrates the orientation of the lens inspection pallets 76 to stage groups of sixteen lenses through the vision inspection machine. One or more vision inspection cameras (not shown) are associated with an inspection channel 77*a,b* for the pallets 76 shown in FIG. 12(*d*). The vision inspection cameras inspect each contact lens location numbered 1–16 as illustrated in smaller type print in FIG. 12(*d*) and which becomes the first data value 51 that is sent from the Vision Inspection machine as discussed above with reference to FIG. 4(*b*). Specifically, vision cameras for inspection channel 77*a* will inspect lens positions 1–8 and vision cameras for inspection channel 77*b* will inspect lens positions 9–16. In view of the predictable way in which the pallets are oriented at vision inspection station, and, in view of the predetermined number of machine cycles necessary to accomplish vision inspection, the vision inspection results are automatically indexed with the original bar code pallet ID (pallets 71*a,b,c,d*) when the control server receives the counter of the vision after receiving the inspection results block 50. To accomplish this, the source memory queue 660 and 660' will be the bar code pallet ID readings taken by bar code scanners 88 and 89, respectively. (FIG. 13(*a*) and (*b*)). Since there is a predetermined amount of machine cycles from the time of bar code pallet identification at the scanners to the time that each lens position of the inspection pallet has been inspected, each cavity result will be associated with the pallet ID index that is offset a predetermined number of memory locations in the respective bar code pallet ID source queue 660 or 660'. For example, as shown in FIG. 12(*d*), the lens inspection results for lens position numbers 5–8 and 13–16 will be associated with bar code scanner 88 memory offset position labelled 622 of source memory queue 660 of FIG. 13(*a*). Likewise, the lens inspection results for lens position numbers 1–4 and 9–12 will be associated with bar code scanner 89 memory offset position labelled 622' of source memory queue 660' of FIG. 13(*b*). Once the vision results are indexed with a bar code pallet ID, they are grouped upon receipt of the vision counter (from the vision server) to form the database record as discussed above and illustrated in FIG. 11.

SCATTERGRAMS

Once all the historical processing data for a particular pallet ID is gathered as records in the database, it is available for further processing and analysis. For instance, as mentioned above, it is desirable to form scattergrams which are charts that relate one variable on the x-axis to one variable on the y-axis. For example, quality measurements are plotted against a process variable to determine if that particular process variable effects the quality and to what degree. The plotted scattergram information further enables selection of the proper operating setpoints for a variable because it readily determined how the quality measurement changes as the value for the process parameter changes.

Figure 14:
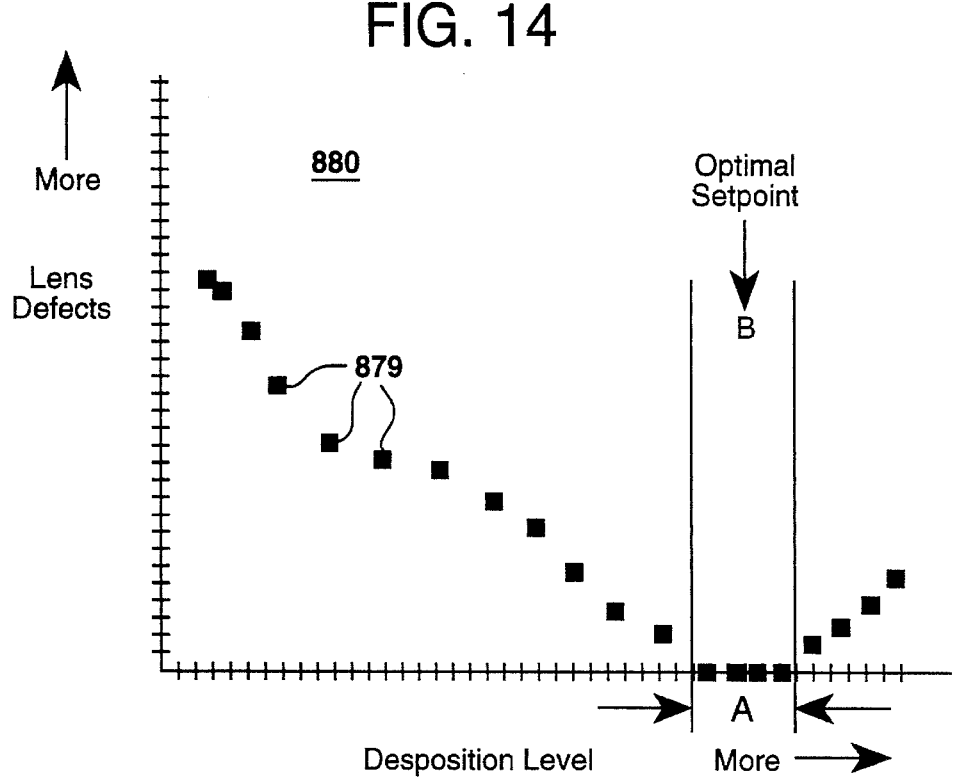
FIG. 14 illustrates a scattergram of inspection results (y-axis) vs. process parameters (x-axis).

FIG. 14 illustrates a scattergram 880 of inspection results (y-axis) vs. process parameters (x-axis). Specifically, a plot has been generated which shows the amount of lens defects for one particular cavity in a pallet as determined by the inspection results out of ALI as a function of front curve monomer deposition level. Alternately, the plot of monomer deposition level may be relative to a particular cavity position on all the recorded pallets. As shown in FIG. 14, the results of this test indicates that the lens manufacturing process must be able to control the monomer deposition level within the front curve mold to within the acceptable range, indicated by arrow A, that has been determined to consistently produce lenses without flaws. As most variations occur in a standard distribution, the first choice for an optimal deposition level setpoint would be in the center of the acceptable range, as indicated by arrow B in FIG. 14. Only a single cavity marker shown as plotting symbol 879 in FIG. 14 is included for clarity. Other types of markers representing other cavities may be included on the same graph. If there are no differences between cavities of the specific pallet, the markers will overlay each other. If one or more cavities are not behaving the same, the markers will not overlay and be visible which would indicate that there exists differences between the cavities that should be corrected so that good lenses may be produced in all cavities.

Figure 16A:
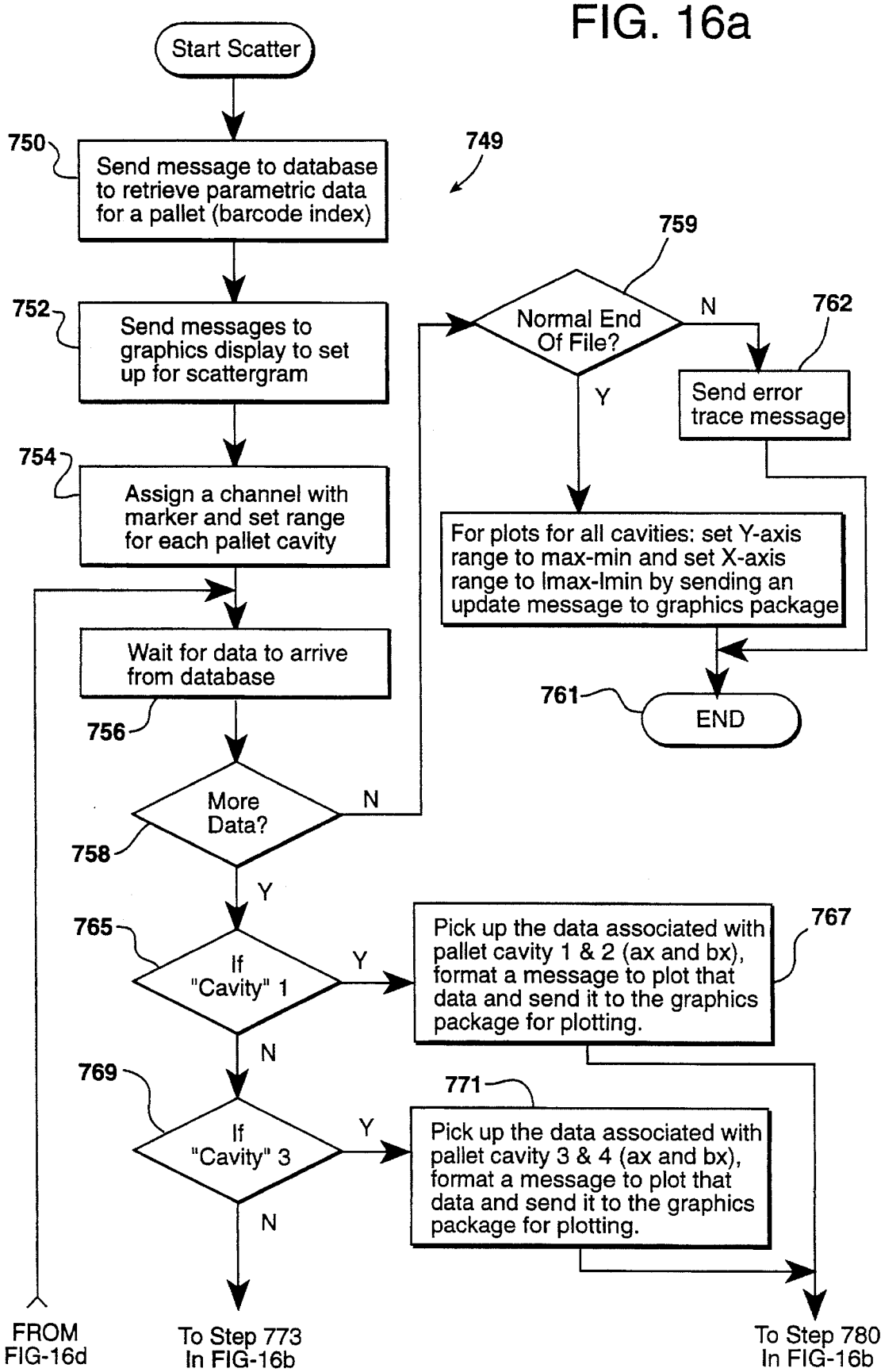
FIGS. 16(a)-16(c) illustrate the process flow for generating a scattergram plot from the data records available in the relational database.
Figure 16B:
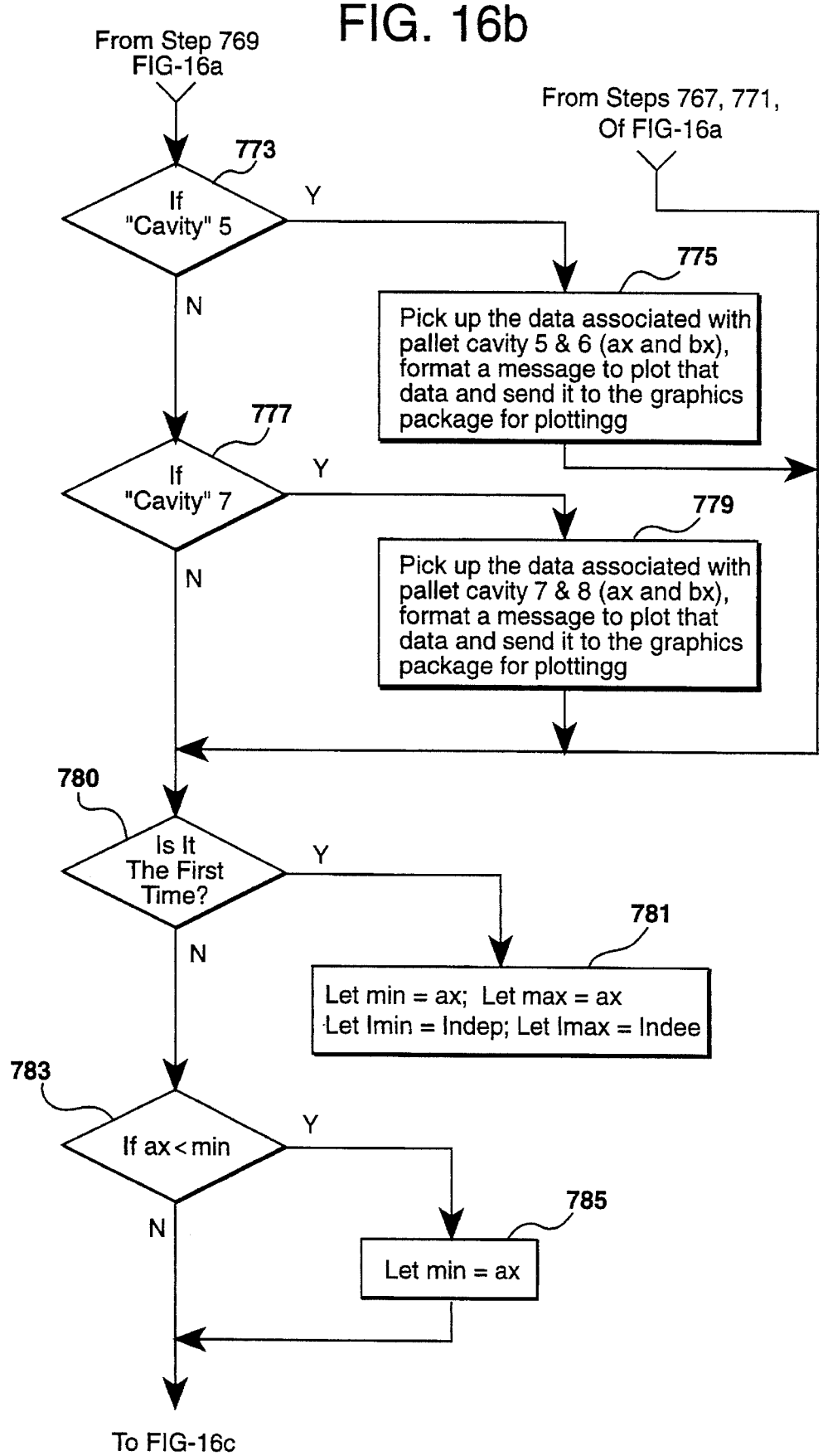
Figure 16C:
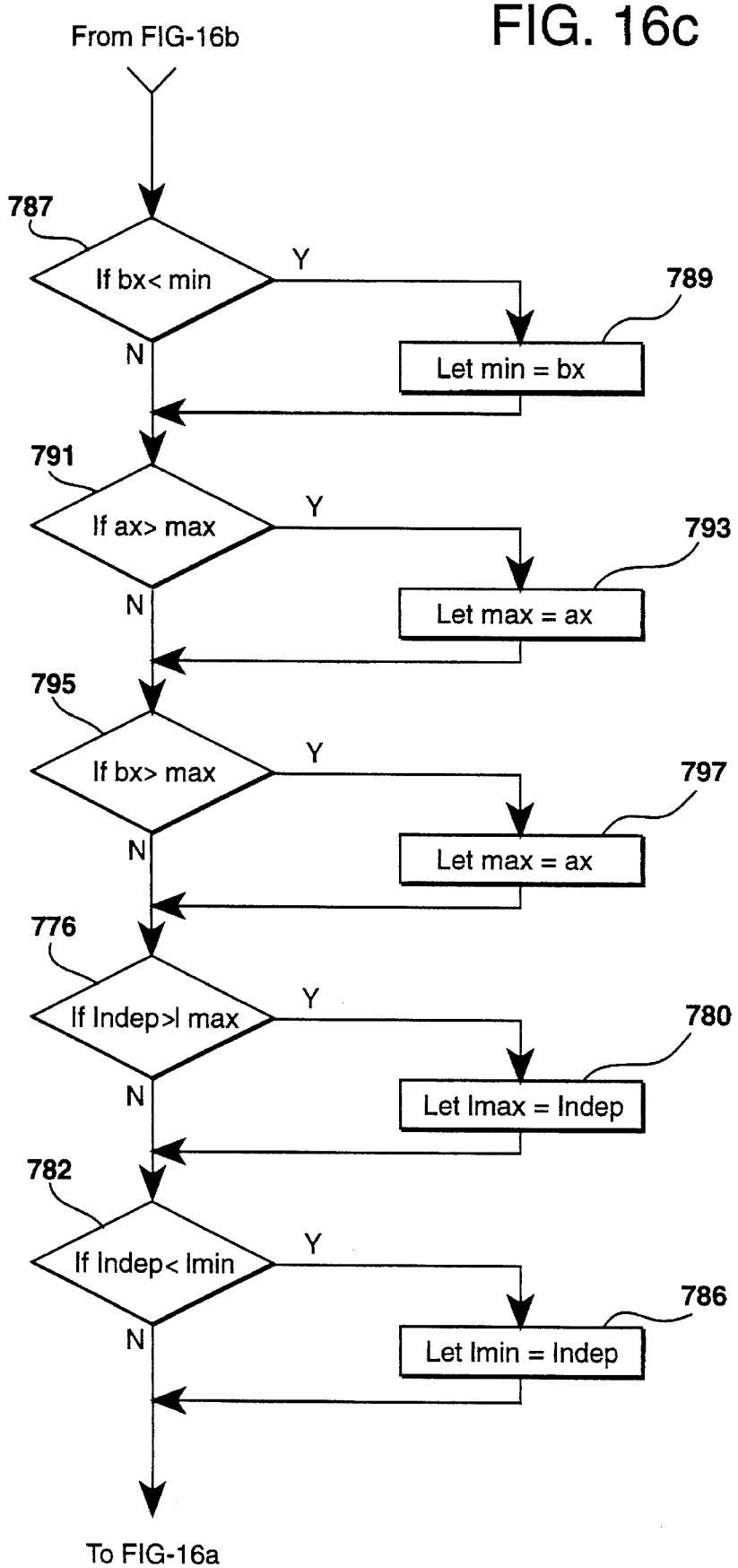

FIGS. 16(*a*)–16(*c*) illustrate the process flow 749 for generating a scattergram plot from the data records available in the relational database. The first step indicated as step 750, is to send the message to the database to retrieve parametric data for a pallet (barcode) index and, at step 752, to send a message to graphs server to set up a display for a scattergram. It should be understood that construction of the procedures to enable proper querying of the database to gather and display the desired reports is known to any programmer skilled in the art of database programming. The next step, indicated as step 754 is to assign a channel with the unique cavity plotting symbol (marker) and other graphic attributes that will become the scattergram display. A spread (range) in the values for each axis may be set-up, for e.g., setting the maximum amount of lens flaw data to ensure that the data points will be plotted within scale. At step 756, the program waits for the data to arrive from the database, and a determination is made at step 758 as to whether there is any more data to arrive. If there is more data to be received at step 758, then a determination is made at step 765 as to whether lens inspection result data for pallet cavity position number 1 is requested to be plotted. If so, then at step 767 the data "ax" and "bx" associated with pallet cavities 1 and 2, respectively, will be sent to the graphics package for plotting and, if the current data value received is the first data value, then a running minimum and maximum of the range may be established at steps 781, et seq. (FIGS. 16(b) and 16(c)). If not, then it is determined at step 769 whether lens inspection result data for pallet cavity position number 3 is requested to be plotted. If so, then at step 771 the data ax and bx associated with pallet cavities 3 and 4, respectively, will be sent to the graphics package for plotting. Next, at step 773, a determination is made as to whether lens inspection result data for pallet cavity position number 5 is requested to be plotted. If so, then at step 775 the data ax and bx associated with pallet cavities 5 and 6, respectively, will be sent to the graphics package for plotting. If not, then it is determined at step 777 whether lens inspection result data for pallet cavity position number 7 is requested to be plotted. If so, then at step 779 the y-axis data ax and bx associated with pallet cavities 7 and 8, respectively, will be sent to the graphics package for plotting. After the appropriate message is sent to the graphics server for plotting the results of a particular cavity as determined at steps 767,771,775 and 779, a determination is made at step 780 as to whether the current data received is the first piece data that is received. If so, the variables min, max, imin, and imax, are initialized at step 781. Variable "indep" represents the independent x-axis variable for the plot and variables "imin" and "imax" represent the minimum and maximum values of variable indep. At step 783, a determination is made as to whether the current retrieved ax data value is a lower limit for the range of y-axis data to be plotted. If ax is less than the min value, then the min value will be set equal to that data point ax at step 785. At step 787, a similar determination is made as to whether the current bx data value is a lower limit for the range of y-axis data to be plotted. If bx the value of the data received, is less than the min value, then the min value will be set equal to that data point bx at step 789. Next, at step 791, a determination is made as to whether the current ax data value is an upper limit for the range of y-axis data to be plotted. If ax the value of the data received, is greater than the current max value, then the max value will be set equal to that data point ax at step 793. At step 795, a similar determination is made as to whether the current bx data value is an upper limit for the range of y-axis data to be plotted. If bx is greater than the max value, then the max value will be set equal to that data point bx at step 797. At step 776, a determination is made as to whether the current indep data value is an upper limit for the range of x-axis data (e.g., monomer deposition level). If indep is greater than the current imax value, then imax is set to indep. A similar determination is made at step 782 as to whether the current indep data value is a lower limit for the range of x-axis data. If indep is less than the current imin value, then imin is set to indep. If it was determined at step 758 that there is more data to be retrieved as requested, then the loop will be repeated and the graphics server will await a new piece of data at step 756.

If there is no more data to be retrieved at step 758, then a determination is made as to whether a normal end of file message has been received as indicated at step 759. If a normal end of file message has been received, then at step 799, the y-axis range, i.e., the value of max–min, is set and the x-axis range, i.e., the value of imax–imin is set, and an appropriate message is sent to the graphics server so that the scattergram may be accurately plotted or displayed. The process will then terminate at step 761. If there was no end of file record received, then an error trace message will be generated at step 762.

HISTOGRAM

The histogram is a graph that displays counts of failures of a specific type (some pass/fail quality measurement). The counts are performed by pallet cavity so that a cavity that performs differently from the others can be isolated (and fixed).

Figure 15:
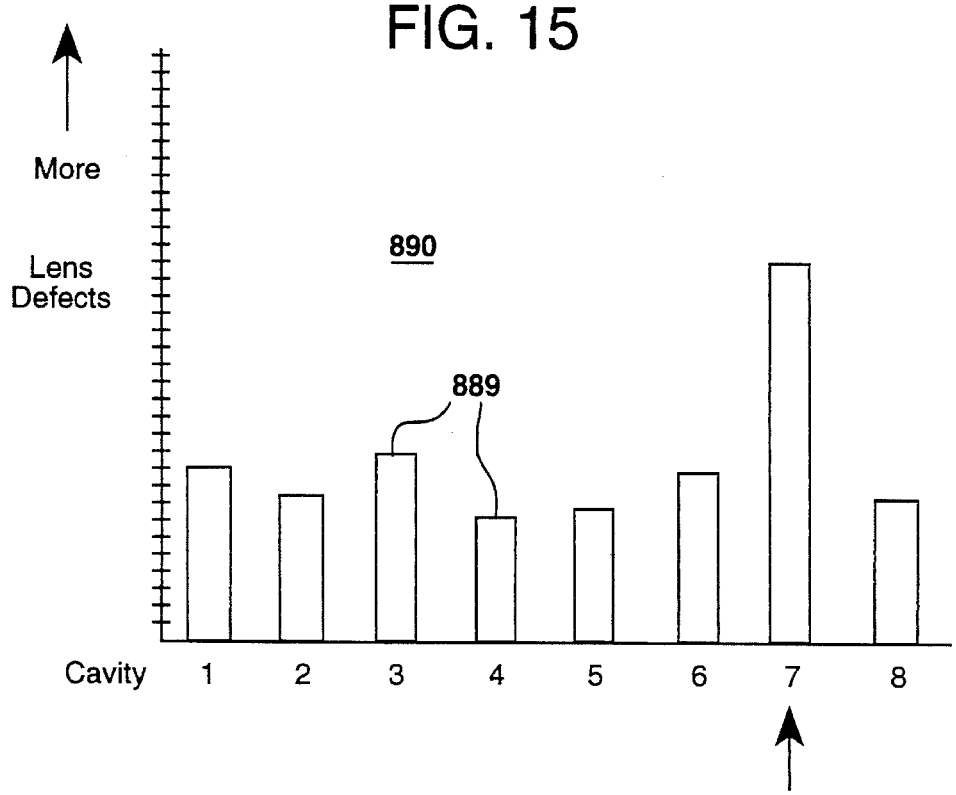
FIG. 15 illustrates a histogram relating the amount of lens defects for a specific cavity position on a specific pallet for multiple passes of the pallet through the line.

FIG. 15 illustrates a histogram 890 relating the amount of lens flaws for a specific cavity position on a specific pallet. Specifically, each bar, 889 represents the number of defects for each cavity of a specific pallet that resulted within a user specified time period. From such a graph, it may be readily determined which cavity position has more defects than the others on the same pallet. A situation such as the graph illustrated in FIG. 15 may indicate that there are contaminants in the cavity number seven (7) as indicated by the arrow.

Figure 17:
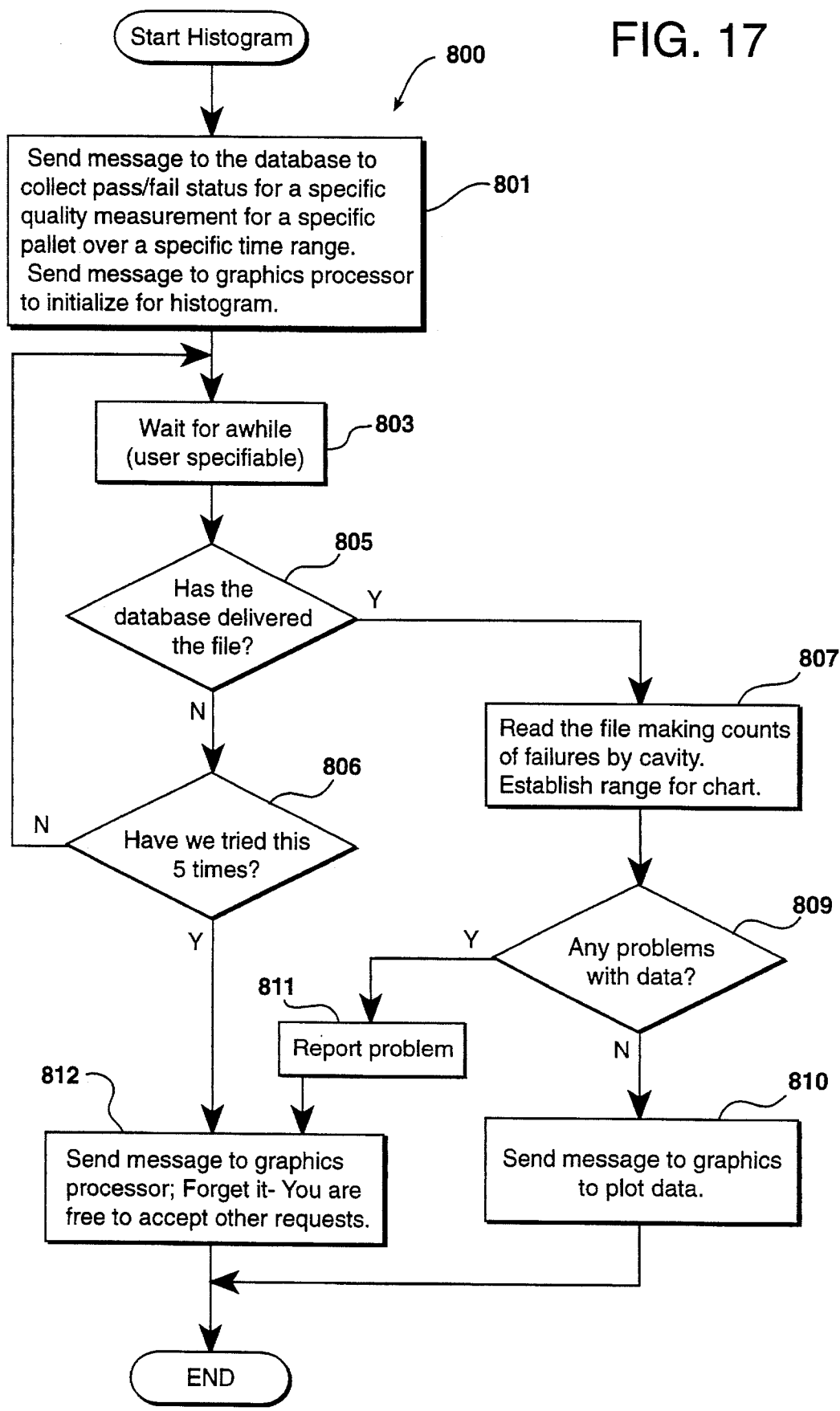
FIG. 17 illustrates the process flow for generating a histogram plot from the group data records available in the relational database.

FIG. 17 illustrates the process flow 800 for generating a histogram plot from the group data records available in the relational database. Step 801 is the step that requests the database to collect pass/fail (inspection result) status for a specific quality measurement for a specific pallet over a specific time range, and to send the data to the graphics server. After waiting a while at step 803, a determination is made at step 805 as to whether the database has delivered the file containing the requested data information. If the file has been delivered, the graphics server will read the file and keep a running total of the failures per cavity, as indicated at step 807. A range will be automatically set so that the data will be accurately plotted. After reading the file sent from the database, a determination is made at step 809 as to whether there are any problems such as not receiving as much data as requested, or, getting an unexpected pass/fail code, for e.g. If a problem is detected, then the problem will be reported at step 811 and a termination message sent to the graphics processor at step 812. If there are no data problems to report then the message to plot the data will be sent to the graphics display to plot the data, as shown in step If the database has not delivered the file at step 805, then the system will wait five times as shown at step 806. If, after the fifth time, the database has not delivered the file, then a message will be sent to the graphics server at step 812 that it is free to accept other graphic display requests.

PROCESS WIDTH HISTOGRAM

The process width distribution histogram is a graph showing how the values of a series of process readings are distributed. A normally-distributed process, for example, will exhibit a bell-shaped histogram plot. This kind of histogram is useful in spotting abnormalities in manufacturing processes or flaws in measurement devices.

Figure 18:
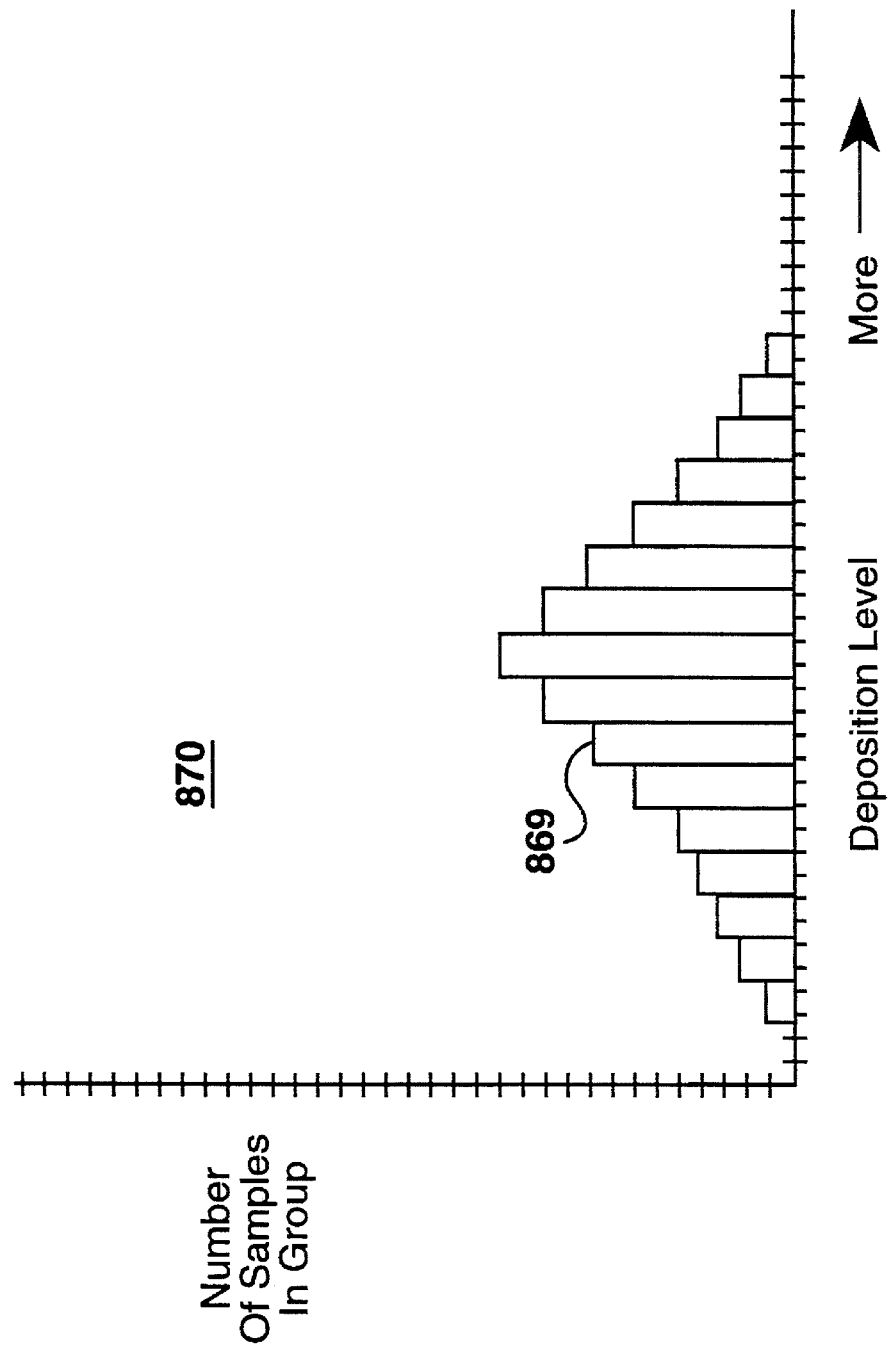
FIG. 18 illustrates a process width histogram that provides an indication of how a particular process parameter (for e.g., monomer deposition level) is behaving.

FIG. 18 illustrates a process width histogram 870 that provides an indication of how a particular process parameter (for e.g., monomer deposition level) is behaving. As shown in FIG. 18, the data is divided up into sixteen (16) equally spaced zones. Each zone is represented by a bar 869, the height of which represents the number of samples that occur in that zone. If the width of the sum of all the histogram bars is the same or smaller than the specification width, then the process can be controlled within the specification tolerance. If the shape of the histogram is that of a bell-shaped curve, then the parameter variation can be said to have a normal distribution.

Figure 19:
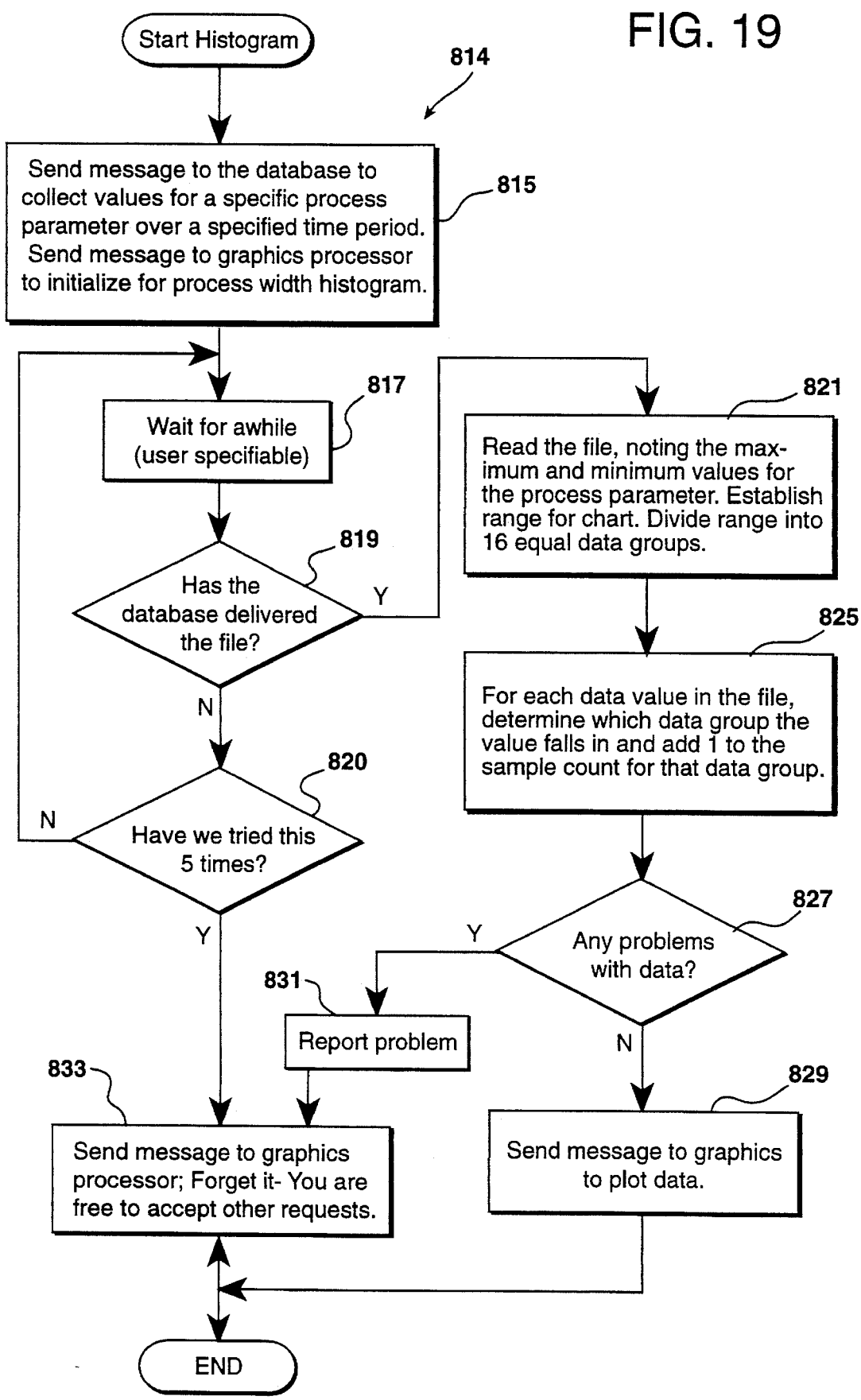
FIG. 19 illustrates the process flow for generating a process width histogram plot from the group data records available in the relational database.

FIG. 19 illustrates the process flow 814 for generating a process width histogram plot from the group data records available in the relational database. Step 815 is the step that requests the database to collect values for a specific process parameter over a specific time period, and to send the data to the graphics server. After waiting a while at step 817, a determination is made at step 819 as to whether the database has delivered the file containing the requested data information. If the file has been delivered, the graphics server will read the file and keep a tally of the maximum and minimum values for a process parameter, as indicated at step 821. A range will be automatically be established from the maximum and minimum values so that the x-axis coordinates will be divided into sixteen (16) equal data groups. At step 825, each data value in the file is read and a determination is made as to which data group the value falls in and increment by one (1) a sample count (not shown) for that particular data group. A determination is then made at step 827 as to whether a normal end of file was encountered. A normal end of file indicates there were no problems reading the data from the database. If a problem is detected, then the problem will be reported at step 831 and a termination message sent to the graphics processor at step 833. If there are no data problems to report then the message to plot the data will be sent to the graphics display to plot the data, as shown in step 829.

If the database has not delivered the file at step 819, then the system will wait five times as shown at step 820. If, after the fifth time, the database has not delivered the file, then a message will be sent to the graphics server at step 833 that it is free to accept other graphic display requests.

STATISTICS SERVER

The statistics server 406 as shown in FIG. 1 is a repository for real-time data values. Data is stored within logical user defined groups or datasets. The power of the stat server is the ability to apply transformations, or "PERFORMS" to the data. Data values when received from control server are automatically tracked for alarm conditions and summarized and the server implements statistical process control and sets and clears the associated alarms. Values from datasets are forwarded to show current trends and animated status screens.

As illustrated in FIG. 6, STATE commands 604 are sent from the Console Server 403 and Graph Server 405 to the Control Server 600. These commands refer to a dataset and optionally to a method name. The commands are used to cue Control Server 600 to issue commands to the Statistics Server 406. These commands direct the Statistics Server 406 to make the appropriate calculations to support a screen and send the results to the active display modules at operator stations 400.

When a method name is given, the STATE command 604 is telling Control Server to send the Statistics Server a pre-defined set of commands (a method) with substitutions made to suit the specific dataset. The method may be thought of as a template for a set of commands to send to the Statistics Server.

The Control Server 600 provides three types of outputs to the Statistics Server 406:

1) The START message 601 to initiate Statistics Server execution during system startup.

2) Source data messages 602, which inform the Statistics Server about new data values. The data is sent to a dedicated Statistics Server mailbox (not shown). The general form of the message is "datasetname =value".

3) Messages that change the way that the Statistics Server processes data, and, that add or remove the destinations for the data produced by the Statistics Server. The primary message types that are sent to the Statistics Processor include: DATASET, which allocates storage in Statistics Server for a named dataset; SINK, which specifies the destination of outgoing data from Statistics Server; PERFORM, which specifies a function that Statistics Server should apply to a dataset; REMOVE, which removes an object from Statistics Server (dataset, sink, perform, etc.); and, CONTROL, which sets alarm range limits for a dataset in the Statistics Server for statistical process control for a dataset.

TIME TRENDING

Any measured or calculated parameter can be plotted versus time as a single trend. Multiple time plots can be compared on a general trend. Fixed time scales are available to show data over minutes, hours, days and weeks.

The statistics server 406 contains a package that allows datasets (a number of samples of the same data source) to be established. Once a dataset has been established, operations to be performed based on some criteria can be setup to happen automatically. Sinks (destinations for produced results) may be dynamically established, for example an operator station for graphing, or another dataset for establishing a history.

For each of the data sources desired to be graphed as a trend over cycles, minutes (10 six second cycles), hours (60 minutes), days (24 hours) and weeks (7 days) a series or cascade of datasets, where "s" is the size, must be created. To accomplish this the sixty (60) most recent values for that dataset must be stored so that they will be available when commanded to be sent to an operator station for graphing or performing some operation, for example:

The process parameter monomer deposition level "DEPO2LEV" is measured once every cycle and fed into the dataset DEPO2LEV s=60 which can hold up to sixty (60) values. Every tenth reading triggers a PERFORM command, described above, to apply an average calculation to the most recent ten (10) values, and feeds the result into the dataset DEPO2LEV/M s=60 which can hold up to sixty values. In turn, every sixtieth reading of DEPO2LEV/M triggers a PERFORM to feed its average into the dataset DEPO2LEV/H s=60. Similarly, every twenty-fourth reading of DEPO2LEV/H triggers a PERFORM to feed its average into the dataset DEPO2LEV/D s=60, and, every seventh reading of DEPO2LEV/D triggers a PERFORM to feed its average into the dataset DEPO2LEV/W s=60. The cascade will look like this:

cycle reading→dataset DEPO2LEV
one minute average→dataset DEPO2LEV/M
sixty minute average→dataset DEPO2LEV/H
one hour average→dataset DEPO2LEV/D
one day average→dataset DEPO2LEV/W, etc..

where M,H,D, and W are zoom factors to be discussed in detail below. To define a sink (a dataset destination) DEPO2LEV/M with the same name as the dataset named DEPO2LEV/M, makes the dynamic creation and removal of the sinks easier to perform in software. Sinks are dynamically created for the operator stations to graph the trend data. The following set of sinks are created at system initialization time and exist to create the Minute, Hour, Day and Week data to be graphed on request:

sink DEPO2LEV/M d=DEPO2LEV/M
sink DEPO2LEV/H d=DEPO2LEV/H
sink DEPO2LEV/D d=DEPO2LEV/D
sink DEPO2LEV/W d=DEPO2LEV/W Last, to create the history samples as the individual data source readings are sent to the statistics server from the Control Server, the following series of actions is defined:
   perform DEPO2LEV f=mean s=DEMP2LEV/M t=10
   perform DEPO2LEV/M f=mean s=DEPO2LEV/H t=60
   perform DEPO2LEV/H f=mean s=DEPO2LEV/D t=24
   perform DEPO2LEV/D f=mean s=DEPO2LEV/W t=7 where the first perform is the command to take the mean (average) of the ten samples that arrive in the dataset DEPO2LEV (the data source readings taken every cycle for the data point DEPO2LEV) and send the result to the sink DEPO2LEV/M which was, in turn, defined (above) to be the dataset DEPO2LEV/M which now stores the history for the minute averages of the data source DEPO2LEV. Similarly, the second perform is the command to take the mean (average) of the 60 samples that arrive in the dataset DEPO2LEV/M (the average readings for each minute taken from the dataset DEPO2LEV/M) and send the result to the sink DEPO2LEV/H which was, in turn, defined to be the dataset DEPO2LEV/H and now stores the history for hourly averages of the data source DEPO2LEV. Again, the third perform is the command to take the mean (average) of the 24 samples that arrive in the dataset DEPO2LEV/H (the average readings for each hour taken from the dataset DEPO2LEV/H) and send the result to the sink DEPO2LEV/D which was, in turn, defined to be the dataset DEPO2LEV/D and now stores the history for daily averages of the data source DEPO2LEV. Finally, the last perform is the command to take the mean (average) of the 7 samples that arrive in the dataset DEPO2LEV/D (the average readings for each day taken from the dataset DEPO2LEV/D) and send the result to the sink DEPO2LEV/W which was, in turn, defined to be the dataset DEPO2LEV/W and now stores the history for weekly averages of the data source DEPO2LEV. Once the datasets, sinks and performs have been defined the calculations will continue to be performed whenever the defined criteria is met for that perform (e.g., 10 samples have arrived in the dataset DEPO2LEV).

Figure 21B:
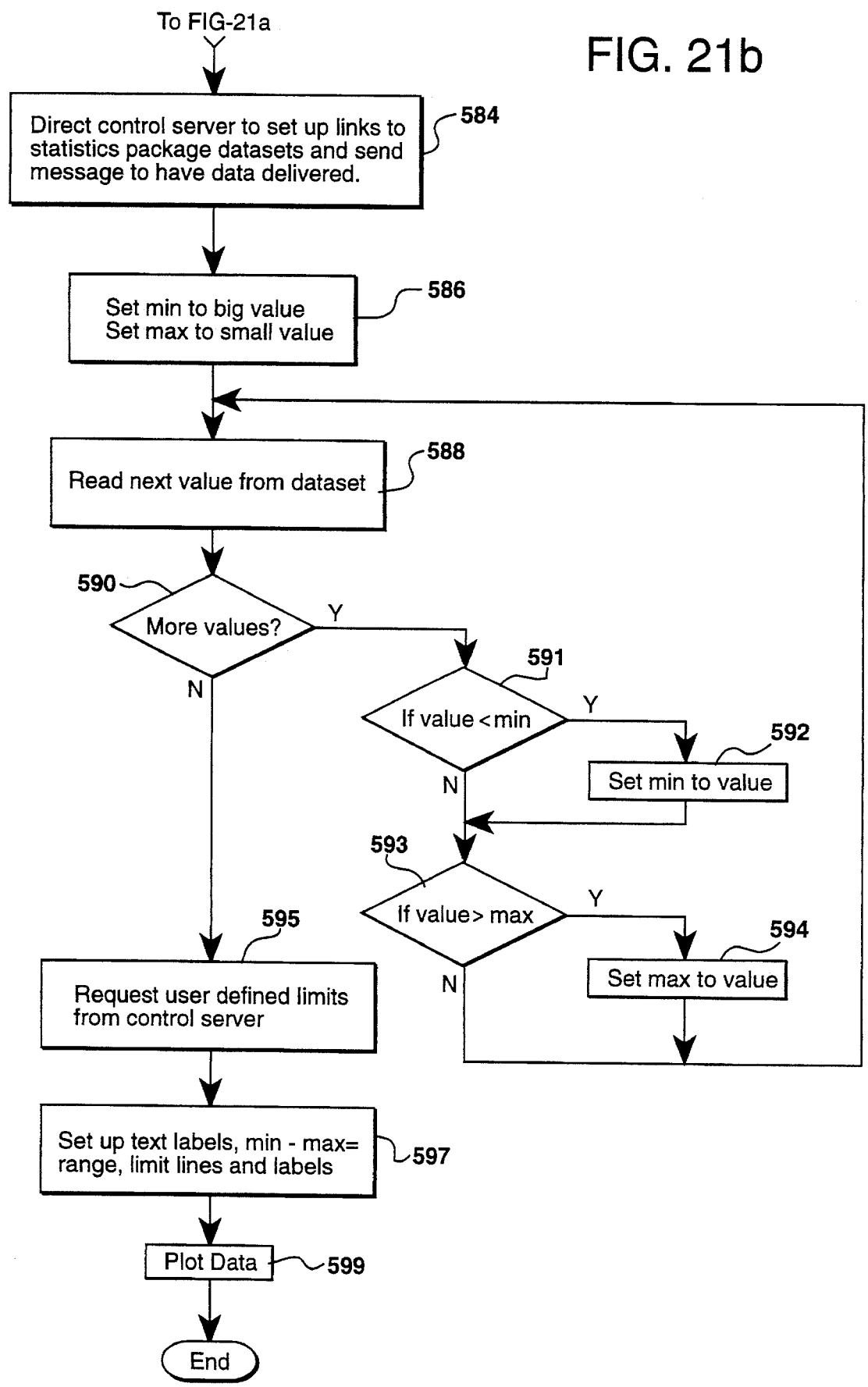

FIG. 21(a) illustrates the sequence 560 for creating a process parameter plot against a fixed time scale to illustrate process parameter trends in the system. At an operator or user interface, an operator may request to view a certain process parameter as it changes in real-time (at the system cycle once every six seconds), or, view a certain process parameter as it changes over a period of time (days, weeks). The entry for a request to generate a trend is a keystroke that may include a zoom_factor" which is a suffix having a value of M, H, D, W and binary value greater than zero. The first step indicated as step 561 is to evaluate the value of the zoom_factor. If the value of the zoom_factor is equal to zero, i.e., no zoom_factor specified, then the dataset is assigned the source or system time scale (once every cycle), as indicated at step 564 in FIG. 21(a). For example, the sixty values contained in the dataset DEPO2LEV described above will be the dataset that will be sent to the graphics server to be plotted. Next, at step 584, suitable links are set up to the statistics package as directed by the control server, and a message is sent to have the data delivered to the statistics package. At step 586, the variables min and max, which are used to set the range for plotting purposes, are initialized. At step 588, each value of the dataset is read and a determination is made at step 590 as to whether there are any more values from the particular dataset.

If there are more values, then the current value of the dataset is compared with the current minimum value (min) of the dataset at step 591. If the current value is less than the minimum value, then the min value is assigned the value of the current dataset value at step 592. If the current value is not less than the minimum value for the dataset, then the current value of the dataset is compared with the current maximum value (max) of the dataset at step 593. If the current value is greater than the maximum value, then the max value is assigned the value of the current dataset value at step 594 and the program is returned to step 588 where the next value is read from the dataset, and steps 590 to 594 are repeated. After there are no more values to be read from the current dataset at step 590, then the user defined limits are requested from the control server at step 595. Next, before plotting the dataset trend data at step 599, the text labels, max_min range, limit lines and labels are set-up at step 597 so that the data will be plotted in a meaningful way.

If the value of the zoom_factor is not equal to zero, i.e., there is a zoom_factor specified, then a determination is made at step 565 as to whether the command is a zoom up command, i.e., whether the fixed x-axis trend should be scaled up to larger time intervals (e.g., hours to days) or a zoom-down command, where it is requested that the fixed trend be scaled down from days to hours, for e.g. If the request is a zoom-up command, then a determination is made as to whether the current zoom-factor status is Days, at step 566; Hours, at step 567; Minutes, at step 568; or, source (real-time) at step 569. If the current status of the zoom_factor is Days, then, the zoom_factor will be incremented to Weeks (W) at step 571; or, if the current status of the zoom_factor is Hours, then, the zoom_factor will be incremented to Days (D) at step 573; or, if the current status of the zoom_factor is Minutes, then, the zoom_factor will be incremented to Hours (H) at step 574; or, if the current status of the zoom_factor is zero (system cycle), then, the zoom_factor will be incremented to minutes (M) at step 576.

If the request is a zoom-down command as determined at step 565 in FIG. 21(a), then a determination is made as to whether the current zoom-factor status is Minutes, at step 577; Hours, at step 578; Days, at step 579; or, Weeks, at step 580. If the current status of the zoom_factor is Minutes, then, the zoom_factor will be decremented to source (system cycle time) (0) at step 581; or, if the current status of the zoom_factor is Hours, then, the zoom_factor will be decremented to Minutes (M) at step 572; or, if the current status of the zoom_factor is Days, then, the zoom_factor will be decremented to Hours (H) at step 582; or, if the current status of the zoom_factor is Weeks, then, the zoom_factor will be decremented to Days (D) at step 583. Once the zoom_factor for the requested process parameter trend graph is determined by the logic as shown in FIG. 21(a), then the dataset to be sent to the statistics server will be the dataset having the source (process data) and the determined zoom_factor. This is shown at step 575 in FIG. 21(a). For instance, in the monomer deposition example described above, the datasets will be d=DEPO2LEV, d=DEPO2LEV/M, d=DEPO2LEV/H, d=DEPO2LEV/D, or, d=DEPO2LEV/W.

Due to the large amount of data found in the on-line and off-line relational databases 202, there are numerous other comparisons and relations that may graphically displayed and charted for manufacturing optimization purposes. For instance, production records that include inspection results for each lens produced along with its process parameters may be accessed and maintained in accordance with FDA regulations. As another example, the system may acquire as data, the sterilizer cycle condition records which include sterilization run success/failure indication, lot number, and sterilization run number from the sterilizer controller (not shown). These files may be stored in the off-line database storage area and be retrieved to analyze the trend of sterilizer performance over a long period of time. Additionally, this data may be accessed to provide equipment and process validation information required by a federal regulatory organization. Other types of operations upon the data including statistical process control may be performed wherein an X bar R chart with dynamic control limits and alarms may be generated; status screens of production summaries, current readings and alarm indicators may be generated for display; an alarm list containing descriptions of active warnings, alarms, and recommendations may be produced; graphic displays in the form of a pareto chart of alarm count and alarm duration by machine, or, a pareto chart of lost lenses by machine component, may be generated to monitor production line machine performance. Examples of alarm conditions include an indexing motor not initialized, or, top chamber vacuum not created at the hydration station, or, an air pressure fault in the hydration station, etc. Other graphic displays may include: events of timestamped log of changes in operation and a time plot displays of cumulative inspection results (yields) may be generated.

These features are allocated to at least two complementary user interfaces (400) available on each station. The engineering console server (not shown) is used for process analysis and optimization. Line operation and machine diagnosis are supported by a production console interface (not shown). A main operator station is enabled to track shift changes and perform alarm acknowledgment, protected by operator long-on (password required).

Pareto Charts

Graphic displays in the form of a pareto chart of alarm count and alarm duration by machine, or, a pareto chart of pallet statuses may be generated. FIG. 22(a) illustrates a pareto chart of an alarm condition by count. The alarm conditions are data values received from the Alarm control server 528 which stores a count of each alarm condition the contact lens production line may experience. As shown in FIG. 22(a), each bar is color coded and represents the frequency of an alarm condition. For instance bar 902a represents a condition where no top chambers at the hydration station exist, and bar 902b represents a motor not initialized. These two alarm conditions represents the most frequent alarms encountered for this particular production run.

Figure 22B:
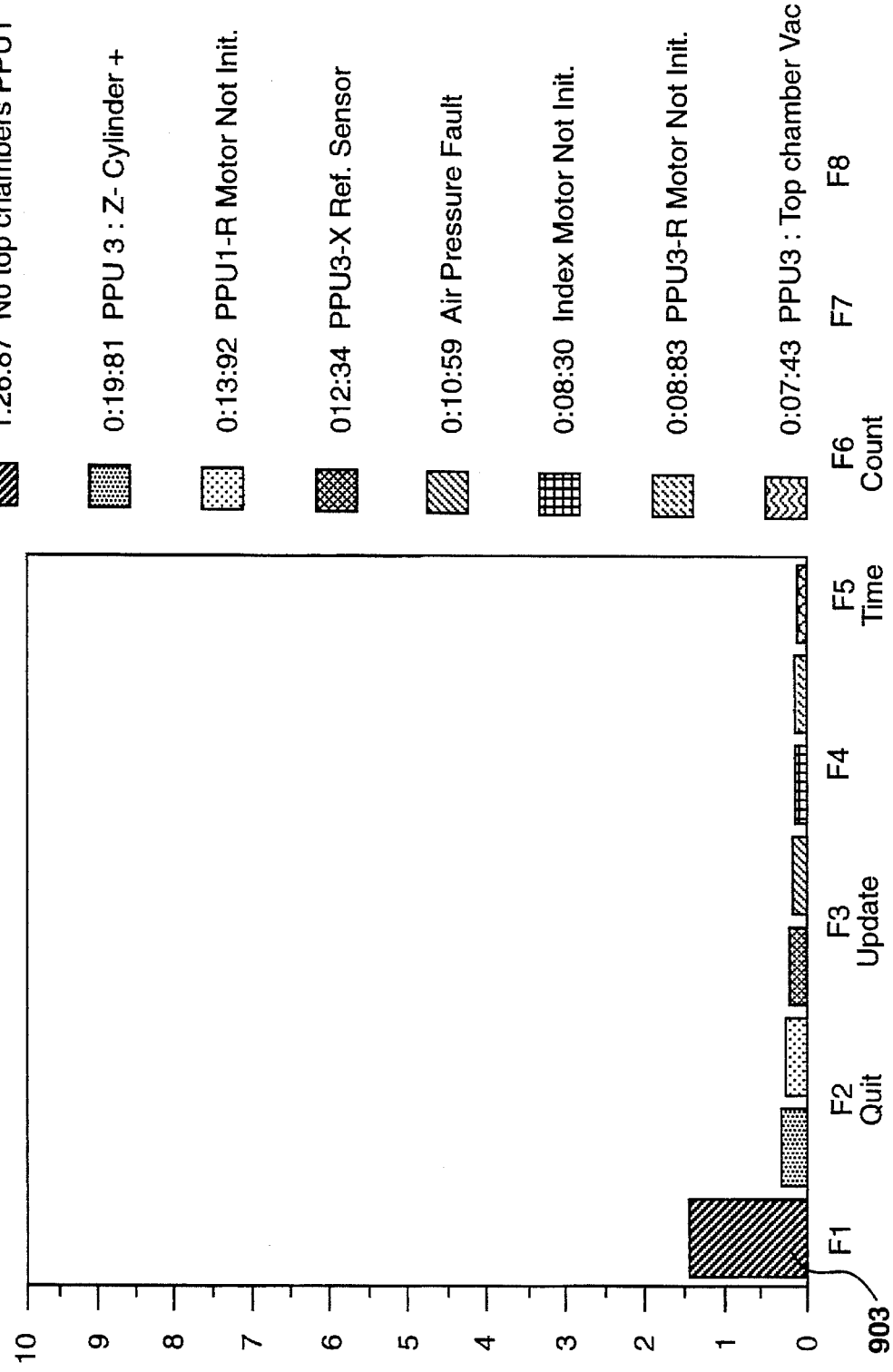
FIG. 22(b) illustrates a Pareto chart of the alarm count by their duration.

FIG. 22(b) illustrates a pareto chart of an alarm condition by time (duration). The alarm conditions by time are data values received from the Alarm control server which stores the duration of time that each alarm condition exists or has existed during contact lens production. As shown in FIG. 22(b), each bar is color coded and represents the duration of an alarm condition. For instance bar 903 represents a condition where no top chambers existed at the hydration station for a period of 1 hr. and 26 minutes.

Figure 22C:
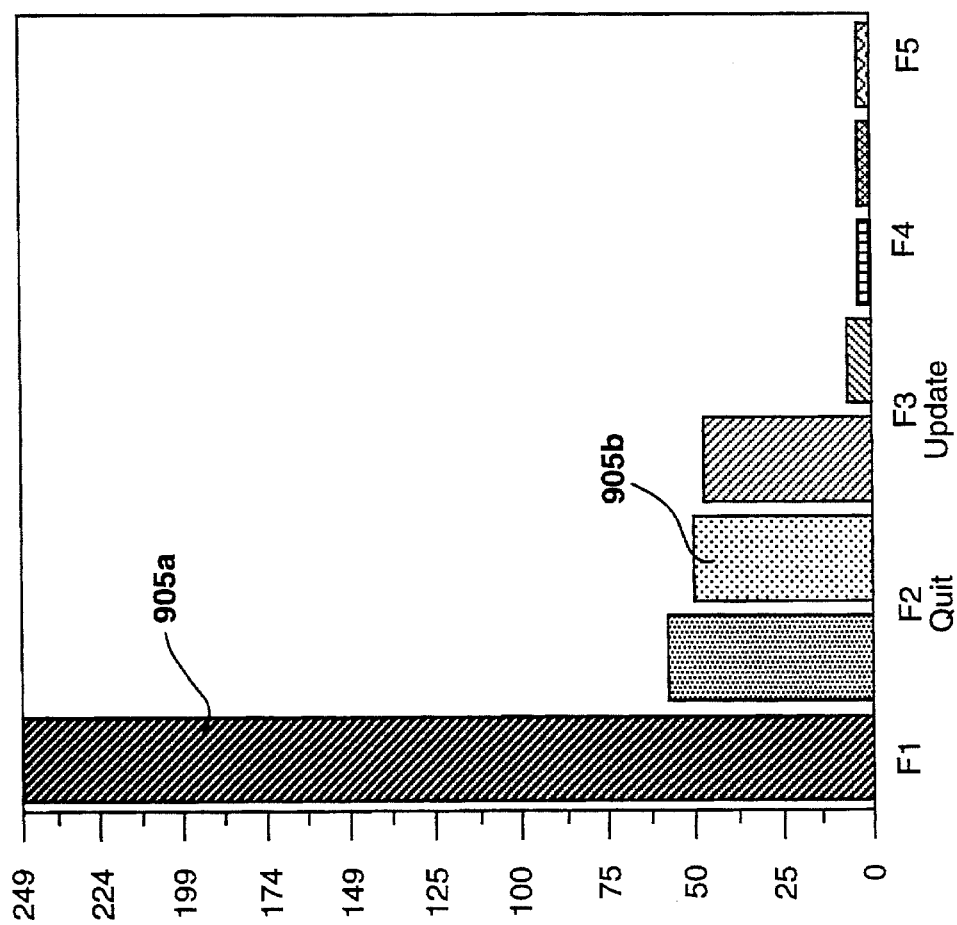
FIG. 22(c) illustrates a Pareto chart of pallet status codes for a particular bar code scanner.

FIG. 22(c) illustrates a pareto chart of pallet statuses (status codes). The chart illustrates the reasons for pallet failures as they pass a particular bar code scanner, for e.g., bar code scanner 86 at the exit of the de-mold assembly. For instance, bar 905a of the chart indicates that 249 pallets were rejected because the excess monomer ring (HEMA ring) was present after de-mold, or, that the back curve lens mold was still present after de-mold (status code −18). Similarly, bar 905b indicates that 50 pallets were rejected because of a fault in the UV polymerization tunnel, i.e., a UV lamp or heater was malfunctional. (status code −4). Note that the frequencies of shown in the Y-axis are sorted in descending order for each of the above-described pareto charts. It should be mentioned that a pareto chart of pallet statuses may be generated for all the bar code scanners in the line.

Figure 23:
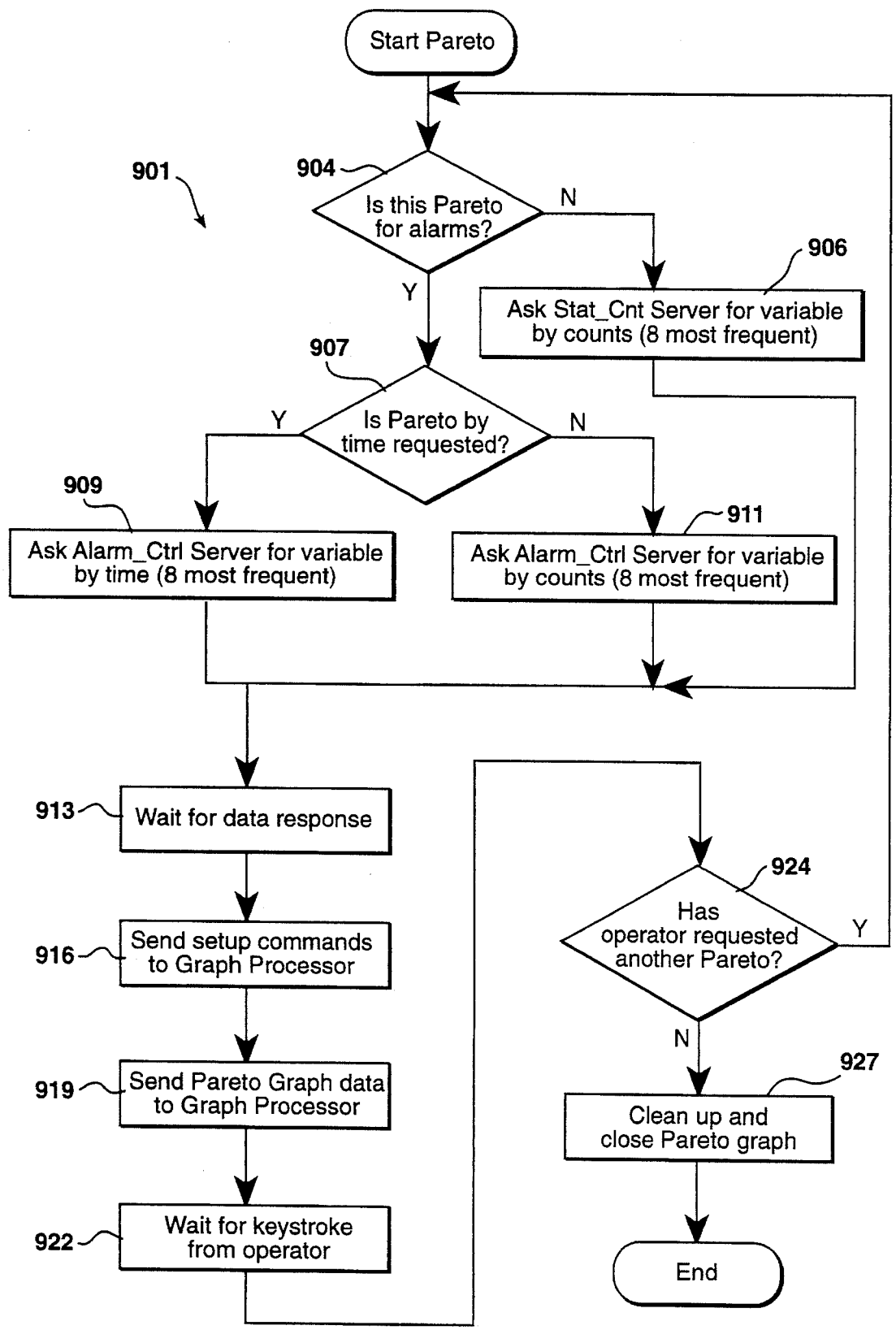
FIG. 23 illustrates the process flow for generating a Pareto chart illustrated in FIGS. 22(a),(b), or (c).

FIG. 23 illustrates the process flow 901 for generating a pareto chart from real time data available from the Alarm_control server and Stat_count server. The first step, indicated at step 904 is a determination of the type of Pareto chart that is requested to be generated and displayed. If the request is to generate a Pareto chart of the alarm conditions (FIGS. 22(a),22(b)), then a determination is made at step 907 as to whether a Pareto by time (duration) is requested. If so, then at step 909 the Alarm Control server is requested to provide data for the top eight most frequent alarms in order of their duration. If a Pareto by alarm count is requested at step 907 then the Alarm Control server is requested to provide data for the top eight most frequent alarms by frequency of occurrence, as indicated at step 911. If the type of Pareto chart requested at step 904 is not for alarms, then it is a request for pallet status codes for a particular bar code scanner, or, all bar code scanners, i.e., the most frequent reasons that pallets are rejected (FIG. 22(c)). If such a request is made, then, at step 906 of FIG. 23, the Stat_count server is requested to provide data for the eight most frequent pallet status conditions for a requested bar code scanner, or, all bar code scanners. The chart of FIG. 22(c) illustrates the most frequent codes requested for bar code scanner 86 (FIG. 20).

After all the data is gathered, which may take an amount of time as shown at step 913, the Pareto chart set-up commands are sent to the graph server to configure a Pareto display as indicated at step 916. Then, the pareto graph data is sent to the graph server at step 919 where the chart is generated and sent to an operator station for display. The graph will remain on-line until the operator requests some action to be taken, for e.g., update the current Pareto display in real time, or, request another type of Pareto chart to be displayed. Thus, at step 922, the system will wait for a keystroke command from the operator, and at step 924 a determination is made as to whether the operator has requested another type of chart to be generated. If another type of Pareto chart is requested to be generated, then the system returns to step 904 in FIG. 23, to determine which type of Pareto chart is being requested. If another type of graph or display is being requested, then the current pareto chart will be closed at step 927 and the graphic display will be exited.

While the invention has been particularly shown and described with respect to the preferred embodiments thereof, it will be understood by those skilled in the art that the foregoing and other changes in form and details may be made therein without departing from the spirit and scope of the invention, which should be limited only by the scope of the appended claims.

We claim:

1. A quality control system for optimizing process parameters in an automated production line for producing contact lenses, said production line having a plurality of process stations, said system comprising:

(a) a plurality of process controllers for controlling one or more process stations, each of said controllers regulating a plurality of process control devices, said devices controlling production parameters used in the automated manufacture of contact lenses at said process station(s), (b) an automated lens inspection means for automatically evaluating each contact lens produced and generating inspection data for each contact lens, (c) polling means for polling each of said process controllers on a frequent basis to acquire process control data for each period, (d) means for generating contact lens data comprising means for correlating said inspection data to said process control data for each contact lens to optimize process parameters used in the production of contact lenses, and (e) a relational database for storing said process control data, said contact lens data and said inspection data received from said correlating means.

2. A quality control system for optimizing process parameters in an automated production line for producing contact lenses, said production line having a plurality of process stations, said system comprising:

(a) a plurality of process controllers for controlling one or more process stations, each of said controllers regulating a plurality of process control devices, said devices controlling production parameters used in the automated manufacture of contact lenses at said process station(s), (b) an automated lens inspection means for automatically evaluating each contact lens produced and generating exception data for each flawed contact lens, (c) polling means for polling each of said process controllers on a frequent basis to acquire process control data for each period, (d) means for generating contact lens data comprising means for correlating said exception data to said process control data for each contact lens to enable tracking and isolation of the process parameters that resulted in the production of flawed contact lenses, and (e) a relational database for storing said process control data, said contact lens data and said exception data received from said correlating means.

3. A quality control system for optimizing process parameters in an automated production line for producing contact lenses, as claimed in claim 1 or 2, wherein said means for correlating will compare predetermined and calculated input parameters with measured real time data derived from said process control data for optimization.

4. A quality control system for optimizing process parameters in an automated production line for producing contact lenses, as claimed in claim 3, wherein said calculated and measured data is compared over time with said inspection data.

5. A quality control system for optimizing process parameters in an automated production line for producing contact lenses, as claimed in claim 1 or 2, wherein each process controller maintains a list of predetermined process parameters, and reports an alarm condition whenever one of said predetermined process parameters is out of a predetermined range.

6. A quality control system for optimizing process parameters in an automated production line for producing contact lenses, as claimed in claim 5, wherein said means for correlating generates a pareto chart of alarm conditions by process control device.

7. A quality control system for optimizing process parameters in an automated production line for producing contact lenses, as claimed in claim 1 or 2, wherein said means for correlating isolates uncontrolled trend values from said process control data.

8. A quality control system for optimizing process parameters in an automated production line for producing contact lenses, as claimed in claim 1 or 2, wherein said means for correlating correlates history trends from multiple time plots developed from said process control data.

9. A quality control system for optimizing process parameters in an automated production line for producing contact lenses, as claimed in claim 1 or 2, wherein said process control data is transmitted to said relational database in groups by said correlating means, and said data is time-stamped at the time said data is sent to said relational data base.

10. A multi-level quality control system for an automated production line for producing contact lenses in palletized batches, said production line having a plurality of process stations, said system comprising:

(a) a plurality of process controllers for controlling one or more process stations at a first control level, each of said controllers regulating a plurality of process control devices, said devices controlling production parameters used in the automated manufacture of contact lenses at said process station(s), each of said controllers generating a reject signal when a pallet of lenses encounters a production parameter that exceeds a predefined range, (b) a plurality of means responsive to said reject signal to remove said pallet from said production line after said signal is generated, (c) an automated lens inspection means for automatically evaluating each contact lens produced and generating exception data for each flawed contact lens that was produced with production parameters that did not exceed said predefined ranges, (d) polling means for polling each of said process controllers and said lens inspection means on a frequent basis to acquire process control data for each period, (e) means for correlating said process control data with contact lens data representing the pallet of contact lenses resident in said process station during said period, and further correlating exception data to said process control data and said contact lens data to optimize process parameters used in the production of contact lenses, (f) a relational database for storing said process control data, said contact lens data and said exception data received from said polling means, 11. A multi-level quality control system for an automated production line for producing contact lenses in palletized batches, said production line having a plurality of process stations, said system comprising:

(a) a plurality of process controllers for controlling one or more process stations at a first control level, each of said controllers regulating a plurality of process control devices, said devices controlling production parameters used in the automated manufacture of contact lenses at said process station(s), each of said controllers generating a reject signal when a pallet of lenses encounters a production parameter that exceeds a predefined range, (b) a plurality of means responsive to said reject signal to remove said pallet from said production line after said signal is generated, (c) an automated lens inspection means for automatically evaluating each contact lens produced and generating exception data for each flawed contact lens that was produced with production parameters that did not exceed said predefined ranges, (d) polling means for polling each of said process controllers and said lens inspection means on a frequent basis to acquire process control data for each period, said polling means correlating said data with contact lens data representing the pallet of contact lenses resident in said process station during said period, (e) a relational database for storing said process control data, said contact lens data and said exception data received from said polling means, (f) a second level data processing means for correlating said exception data to said process control data and said contact lens data to isolate production line components responsible for the production of one or more flawed contact lenses during each cycle of operation.

12. A multi-level quality control system as claimed in claim 10 or 11, wherein said contact lenses are molded in molds carried in recesses formed in said pallets, and said second level data processing means isolates specific pallets which have one or more recesses which have contributed to the production of flawed contact lenses.

13. A multi-level quality control system as claimed in claim 10 or 11, wherein said lens inspection means generates data for each lens inspected, and said correlation includes a cumulative record of lens inspections and one or more process control parameters.

14. A multi-level quality control system for an automated production line for producing molded contact lenses in palletized batches, said production line having a plurality of process stations, including at least one injection station for molding mold parts used to mold said contact lenses, said system comprising:

(a) a plurality of process controllers for controlling one or more process stations and said injection station at a first control level, each of said controllers regulating a plurality of process control devices used in said process stations and said injection station, said devices controlling production parameters used in the automated manufacture of contact lenses at said station(s), each of said controllers generating a reject signal when a pallet of mold parts or a pallet of molded lenses encounters a production parameter that exceeds a predefined range, (b) a plurality of means responsive to said reject signal to remove said pallet from said production line after said signal is generated, (c) an automated lens inspection means for automatically evaluating each contact lens produced and generating exception data for each flawed contact lens that was produced with production parameters that did not exceed said predefined values, (d) polling means for polling each of said process controllers and said lens inspection means on a frequent basis to acquire process control data for each period, said polling means correlating said data with contact lens data representing the pallet of contact lenses resident in said process station during said period, (e) a relational database for storing said process control data, said contact lens data and said exception data received from said polling means, (f) a second level data processing means for correlating said exception data with said process control data for said injection station(s) and process control data from said process stations to optimize process parameters used in the production of contact lenses.

15. A multi-level quality control system as claimed in claim 14, wherein said process control data from said injection station is correlated with data relating to the configuration of said pallet to enable correlation of said exception data to individual mold cavities at said injection station(s).

16. A multi-level quality control system as claimed in claim 14, wherein one of said process control stations regulates the amount of a monomer that is dosed into said mold to form a contact lens, and said process control data from said injection station is used by said process control device at said dosing station in dosing said monomer into said mold to form said lens.

17. A multi-level quality control system as claimed in claim 14, wherein said contact lenses are molded in molds carried in recesses formed in a predetermined array on said pallets and said molds have been formed at said injection station in an array of cavities, and said second level data processing means isolates specific injection mold cavities which contribute to the production of flawed contact lenses.

18. A quality control system for optimizing process parameters in an automated production line for producing contact lenses, as claimed in claim 14, wherein process control parameters for each pallet of lenses is archived in said relational data base.

19. A quality control system for optimizing process parameters in an automated production line for producing contact lenses, as claimed in claim 2 or 10 or 11 or 14, wherein said automated lens inspection means generates an inspection result for each lens, and said inspection result is correlated with said contact lens data and said process control data in said relational data base.

20. A method of optimizing control of process parameters in an automated production line for producing contact lenses, when said production line has a plurality of inter-related production stations, said method comprising:

(a) controlling one or more production stations automatically with one or more primary level controllers which regulate a plurality of process control devices to thereby control a plurality of production parameters used in the automated manufacture of contact lenses, (b) automatically evaluating each contact lens produced and generating visual inspection data for each contact lens produced, (c) polling each of said primarily level controllers on a frequent basis to acquire process control data for each period, and then correlating said process control data with assigned contact lens data which represents the contact lenses resident in said production station during said period, (d) storing said process control data, said contact lens data and said visual inspection data received from said polling means in a relational data base, (e) correlating said visual inspection data to said process control data and said contact lens data to optimize process parameters used in the production of contact lenses.

21. A method of optimizing control of process parameters in an automated production line for producing contact lenses, as claimed in claim 20, where said method further includes the step of generating exception data for each contact lens which fails said visual inspection, and then correlating said exception data to said process control data and said contact lens data to enable tracking and isolation of the process parameters that resulted in the production of flawed contact lenses.

22. A method of optimizing control of process parameters in an automated production line for producing contact lenses, as claimed in claim 20, where said method further includes the step of storing predetermined and calculated input parameters and comparing said calculated input parameters with measured real time data derived from said process control data.

23. A method of optimizing control of process parameters in an automated production line for producing contact lenses, as claimed in claim 20, where said method further includes the step of comparing said calculated and said measured data over time with said exception data.

24. A method of optimizing control of process parameters in an automated production line for producing contact lenses, as claimed in claim 20, where said method further includes the step of maintaining a list of predetermined process parameters in each of said primary level controllers and reporting an alarm condition whenever one of said predetermined process parameters exceeds said predetermined parameter.

25. A method of optimizing control of process parameters in an automated production line for producing contact lenses, as claimed in claim 20, where said method further includes the step of generating a pareto chart of alarm conditions by process control devices.

26. A method of optimizing control of process parameters in an automated production line for producing contact lenses, as claimed in claim 20, where said method further includes the step of isolating uncontrolled trend values from said process control data.

27. A method of optimizing control of process parameters in an automated production line for producing contact lenses, as claimed in claim 20, where said method further includes the step of correlating history trends from multiple time plots developed from said process control data.

28. A method of optimizing control of process parameters in an automated production line for producing contact lenses, as claimed in claim 20, where said method further includes the step of transmitting said process control data to said relational database in data groups and time-stamping said data groups at the time said data is stored in said relational data base.

29. A method of optimizing control of process parameters in an automated production line for producing contact lenses, as claimed in claim 20, wherein said contact lenses are molded in molds carried pallets having a recess for each mold, and said correlating step includes the step of isolating specific pallets which have one or more recesses which have contributed to the production of flawed contact lenses.

30. A method of optimizing control of process parameters in an automated production line for producing contact lenses, as claimed in claim 29, wherein said molds are formed in an array of mold cavities in an injection molding device that is included in said production line, and said correlating step links said contact lens data with data relating to said array to enable correlation of said inspection data to individual mold cavities.

* * * * *